United States Patent [19]

Reeders et al.

[11] Patent Number: 5,731,192
[45] Date of Patent: Mar. 24, 1998

[54] COLLAGEN COL4A6: GENE, PROTEIN AND METHOD OF DETECTING COLLAGEN DEFICIENCY

[75] Inventors: Stephen T. Reeders, Hamden, Conn.; Jing Zhou, Boston, Mass.

[73] Assignee: Yale University, New Haven, Conn.

[21] Appl. No.: 494,168

[22] Filed: Jun. 23, 1995

Related U.S. Application Data

[63] Continuation of Ser. No. 112,465, Aug. 27, 1993, abandoned.

[51] Int. Cl.$^6$ ............................ C12N 15/63; C07H 21/04
[52] U.S. Cl. ................................. 435/320.1; 536/23.5
[58] Field of Search ........................ 435/320.1; 536/23.5

[56] References Cited

U.S. PATENT DOCUMENTS

| | | | |
|---|---|---|---|
| 5,114,840 | 5/1992 | Tryggvason | 435/6 |
| 5,354,690 | 10/1994 | Tryggvason | 436/501 |
| 5,424,409 | 6/1995 | Reeders | 536/23.5 |

OTHER PUBLICATIONS

Barker et al. "Identification of Mutations in the COL4A5 Collagen Gene in Alport Syndrome," *Science* 248: 1224–1227 (1990).

Zhou et al. "Single Base Mutation in α5(IV) Collagen Chain Converting a Conserved Cysteine to Serine in Alport Syndrome," *Genomics* 9: 10–18 (1991).
Antignac et al. "Alport Syndrome and diffuse leiomyomatosis: Deletions in the 5' end of the COL4A5 collagen gene," *Kidney Int.* 42: 1178–1183 (1992).
Tryggvason et al. "Molecular genetics of Alport Syndrome," *Kidney Int.* 43: 38–44 (1993).
Cochat et al. "Diffuse Leiomyomatosis in Alport Syndrome," *Journ. of Pediatrics* 113(2):339–343 (1988).
Netzer et al. "Deletions of the COL4A5 gene in patients with Alport syndrome," *Kidney Int.* vol. 42: 1336–1344 (1992).
Zhou et al. (1993) "Deletion of the paired alpha5(IV) and alpha6(IV) collagen genes in inherited smooth muscle tumors" Science. 261:1167–1169, Aug. 1993.
Anderson, W. French (1994) "Gene Therapy for Genetic Diseases" *Human Gene Therapy* 5: 281–2.

*Primary Examiner*—Robert A. Wax
*Assistant Examiner*—Kawai Lau
*Attorney, Agent, or Firm*—Foley & Lardner

[57] ABSTRACT

A type IV collagen polynucleotide molecule, COL4A6, encoding α6(IV) polypeptide molecule, is identified on the X chromosome and expressed particularly in basement membranes. Genetic alteration of COL4A6 is associated with Alport's syndrome, a disease of basement membranes. Assays which detect an alteration of collagen α6(IV), or the polynucleotide molecules encoding it, are useful in determining pathologies associated with Alport's syndrome.

8 Claims, 21 Drawing Sheets

FIG. IA

```
1   AATTCCGGTCCCTGGGCTGCTGTCTCTTTACCTTTCCAGCTGCTCACAGAACAGAGAGT   60
    TTAAGGCCAGGGACCCGACGACAGAGAAATGGAAGGTCGACGAGTGTCTTGTCTCTCA
    I  P  V  P  G  L  L  V  F  F  T  F  Q  L  L  T  E  Q  R  V

61  TTCTACATACAAGCAGAAGATGTGAAAATAAAGTATATGCTTATAAA              120
    AAGATGTATGTTCGTCTTCTACACTTTATAACCTTATTATTTCATATACGAATATTT
    S  T  Y  K  Q  K  M  *  K  Y  W  E  *  I  K  Y  M  L  I  N

121 CAAGTTGTGGCTCCTGGTTACGTTGTGCCTGACCGAGAACTGGCAGCAGCGGGAGA     180
    GTTCAACACCGAGGACCAATGCAACACGGACTGGCTCCTTGACCGTCGTCGCCCCTCT
    K  L  W  L  L  V  T  L  C  L  T  E  E  L  A  A  A  G  E

181 GAAGTCTTATGGAAAGCCATGTGGGGGACAGGACTGCAGTGGGAGCTGTCAGTGTTTCC  240
    CTTCAGAATACCTTTCGGTACACCCCCTGTCCTGACGTCACCCTCGACAGTCACAAAGG
    K  S  Y  G  K  P  C  G  G  Q  D  C  S  G  S  C  Q  C  F  P

241 TGAGAAAGGAGCGGAGACGGAGACCTGGACCAATTGGAATTCAAGGCCCAACAGTCCTCA 300
    ACTCTTTCCTCGCTCCTGCCTCTGCCTGGTTAACCTTAAGTTCCGGGTTCCAGGAGT
    E  K  G  A  R  G  R  P  G  P  I  G  I  Q  G  P  T  G  P  Q

301 AGGATTCACTGGCTCTACTGGTTTATCGGATTGAAAGGAGAAAGGGGTTTCCCAGCCT    360
    TCCTAAGTGACCGAGATGACCAAATAGCCCTAACTTTCCTCTTTCCCAAAGGGTCCGGA
    E  K  G  A  R  G  R  P  G  P  I  G  I  Q  G  P  T  G  P  Q
```

```
       G  S  F  K  G  I  K  G  D  P  G  L  P  G  L  D  G  I  T  G
661    CCCACAAGGAGGACCACCCGGATTCCCTGGACCTGTAGGACCTGCAGGACCACCAGGATTACA    720
       P  Q  G  A  P  G  F  P  G  A  V  G  P  A  G  P  P  G  L  Q
721    GGGTGTTCCTCGTGGGCCTAAAGGACCTCGACATCCTGGACGTCCTGGTGTCCTAATGT    780
       P  Q  G  A  P  G  F  P  G  A  V  G  P  A  G  P  P  G  L  Q
       AGGTCCTCCAGGCCCTCCAGGGCCTCCTGGTCCTCTGGAGGACTACCTTATACCCCGATCCAAAAGT
       G  P  P  G  P  P  G  P  L  G  P  D  G  N  M  G  L  G  F  Q
781    TCCAGGAGGTCCCGGAGGACCAGGACCAGGAGAACCAGGACTACCTTATACCCCGATCCAAAAGT    840
       G  P  P  G  P  P  G  P  L  G  P  D  G  N  M  G  L  G  F  Q
       AGGAGAAAGGAGTCAAGGGGATGTTGGCCCTCCCAGCAGGACCTCCACCATC
       G  E  K  G  V  K  G  D  V  G  L  P  G  P  A  G  P  P  P  S
841    TCCTCTCTTTCCTCAGTTCCCCTACAACCGGATTCATGGGATCCCCAAAGGAAGAAAGGATCCAAGGGTGAACC    900
       G  E  K  G  V  K  G  D  V  G  L  P  G  P  A  G  P  P  P  S
       TACTGGAGAGCTGGAATTCATGGGATTCCCCAAAGGAAGAAAGGATCCAAGGGTGAACC
       I  G  E  L  E  F  M  G  F  P  K  G  K  K  G  S  K  G  E  P
       ATGACCCTCGACCTTAAGTACCCTAAGGGGTTTCCCTTCTTTCCTAGGTTCCCACTTGG
       AGGGCCTAAGGGTTTCCAGGCATAAGTGCCCTTCCCGGCCTTCCCAGGGAACTAC
```

FIG. 1D

```
901  AGGGCCTAAGGGTTTTCCAGGCATAAGTGGCCCTTCCCGGGCCTTGGAACTAC
     ----+----|----+----|----+----|----+----|----+----|----+----|
     TCCCGGATTCCCAAAAGGTCCGTATTCACCGGGAGGTCCGAAGGGCCCGGAACCTTGATG  960
       G  P  K  G  F  P  G  I  S  G  P  P  G  F  P  G  L  G  T  T

961  TGGAGAAAAGGGAGAAAAGGAGAAAAGGGAATCCCTGGTTTGCCAGGACCTAGGGTCC
     ----+----|----+----|----+----|----+----|----+----|----+----|
     ACCTCTTTTCCCTCTTTTCCCTCTTTCCCTTAGGGACCAAACGGTCCTGGATCCCCAGG  1020
       G  E  K  G  E  K  G  E  K  G  I  P  G  L  P  G  P  R  G  P

1021 CATGGGTTCAGAAGGAGTCCAAGGCCCTCCAGGCAACAGGGCAAGAAAGGACCCTGGG
     ----+----|----+----|----+----|----+----|----+----|----+----|
     GTACCCAAGTCTTCCTCAGGTTCCGGGAGGTCCGGGAGGTCCGTTGTCCCGTTCTTTCCTGGGACCC  1080
       M  G  S  E  G  V  Q  G  P  P  G  Q  Q  G  K  K  G  T  L  G

1081 ATTTCCTGGGCTTAATGGATTCCAAGGAATTGAGGGTCAAAAGGTGACATTGGCCTGCC
     ----+----|----+----|----+----|----+----|----+----|----+----|
     TAAAGGACCCGAATTACCTAAGGTTCCTTAACTCCCAGTTTTCCACTGTAACCGGACGG  1140
       F  P  G  L  N  G  F  Q  G  I  E  G  Q  K  G  D  I  G  L  P

1141 AGGCCCAGATGTTTTCATCGATATAGATGGTGCTGTGATCTCAGGTAATCCTGGAGATCC
     ----+----|----+----|----+----|----+----|----+----|----+----|
     TCCGGGTCTACAAAAGTAGCTATATCTACCACGACACTAGAGTCCATTAGGACCTCTAGG  1200
       G  P  D  V  F  I  D  I  D  G  A  V  I  S  G  N  P  G  D  P

TGGTGTACCTGGCCCTCCCAGGCCCTTAAAGGAGATGAAGGCATCCAAGGCCTACGTGGCCC
```

FIG. IE

```
1201  ACCACATGGACCGGAGGGTCCGGAATTCCTCTACTTCCGTAGGTTCCGGATGCACCGGG  1260
        G  V  P  G  L  P  G  L  K  G  D  E  G  I  Q  G  L  R  G  P
      TTCTGGTGTCCCTGGATTGCCAGCATTATCAGGTGTCCCAGGAGCCCTAGGCCTCAGGG

1261  AAGACCACAGGACCTAACGGTCGTAATAGTCCACAGGTCCTCCGGATCCCGGAGTCCC   1320
        S  G  V  P  G  L  P  A  L  S  G  V  P  G  A  L  G  P  Q  G
      ATTTCCAGGGCTGAAGGGGACCAAGGAAACCCAGGCCGTACCACAATTGGAGCAGCTGG

1321  TAAAGGTCCCGACTTCCCCCTGGTTCCTTTGGGTCCCGGCATGGTGTTAACCTCGTCGACC 1380
        F  P  G  L  K  G  D  Q  G  N  P  G  R  T  T  I  G  A  A  G
      CCTCCCTGGCAGAGATGGTTGCCAGCCCACCAGGCCACCACTGGCCACTAGTCCAGA

1381  GGAGGGACCGTCTCTACCAACGTCCAGTGTCCAGTGGTCCGGTGGTGGTCCGGATCAGGTCT 1440
        L  P  G  R  D  G  L  P  G  P  P  G  P  P  G  P  P  S  P  E
      ATTTGAGACTGAAACTCTACACAACAAGAGTCAGGGTTCCCTGTCTCCGAGGAGAACA

1441  TAAACTCTGACTTTGAGATGTGTTTCTCAGTCCCAAGGACCAGAGGCTCCTCTTGT     1500
        F  E  T  E  T  L  H  N  K  E  S  G  F  P  G  L  R  G  E  Q
      AGGTCCAAAGGAAACCTAGGCCTCAAAGGAATAAAAAGGAGACTCAGTTTCGTGCTTG

1501  TCCAGGTTTCCTTTGGATCCGGAGTTTCCTTATTTTCCTCTGAGTCCAAAGACACGAAC  1560
```

FIG. 1F

```
          G  P  K  G  N  L  G  L  K  G  I  K  G  D  S  G  F  C  A  C
     1561 TGACGGTGGTGTGTTCCAACACTGGAACCCGGGAACCAGGCCCCACCTGTCCATGGGG 1620
          ACTGCCACCACAAGGGTTGTGACCTTGGGCCCTTGGTCCGGGTGGACCAGTACCCC
          D  G  V  P  N  T  G  P  P  G  E  P  P  G  P  P  G  P  W  G
     1621 TCTCATAGGCCTTCCAGGCCTTAAAGGAGCCAGAGGAGATCGAGGCTCTGGGGTGCACA 1680
          AGAGTATCCGGAAGGTCCGGAATTTCCTCGGTCTCCTCTAGCTCCGAGACCCCACGTGT
          L  I  G  L  P  G  L  K  G  A  R  G  D  R  G  S  G  A  Q
     1681 GGGCCCCAGCAGGGCTCCCAGAGTCCGAATCAACCCGGAAGAAGTCCTGGTTTCCTTT 1740
          CCCGGGGTCGTCCCGAGGGTCTCAGGCTTAGTTGGGCCTTCTTCAGGACCAAAGGAAA
          G  P  A  G  A  P  G  L  V  G  P  L  G  P  S  G  P  K  G  K
     1741 GAAGGGGGAACCAATTCTCAGTACAATCCAAGGAATGCCAGGAGATCGGGGTGATTCTGG 1800
          CTTCCCCCTTGGTTAAGAGTCATGTTAGGTTCCTTACGGTCCTCTAGCCCCACTAAGACC
          K  G  E  P  I  L  S  T  I  Q  G  M  P  G  D  R  G  D  S  G
     1801 CTCCCAGGGCTTCCGTGTGTAATAGGAGAACCAGGCAAGGACGGAGTACCAGGTTTACC 1860
          GAGGGTCCCGAAGGCACCACATTATCCTCTTGGTCCGTTCCTGCCTCATGGTCCAAATGG
          S  Q  G  F  R  G  V  I  G  E  P  G  K  D  G  V  P  G  L  P
```

FIG. 1G

```
1861 AGGTCTGCCAGGCCTTCCGGGTGATGGTGGACAGGGCTTCCCAGTGAAAAGGGGTTACC
     ----+----+----+----+----+----+----+----+----+----+----+----+  1920
     TCCAGACGGTCCGGAAGGCCACTACCACCTGTCCCGAAGGTCCACTTTTCCCCAATGG
       G  L  P  G  D  G  G  Q  G  F  P  G  E  K  G  L  P

1921 TGGACTTCCTGGTGAAAAAGGCCATCCTGGTCCACCTGGCCTCCCCAGGAAATGGGTTACC
     ----+----+----+----+----+----+----+----+----+----+----+----+  1980
     ACCTGAAGGACCACTTTTTCCGGTAGGACCAGGTGGACCGGAGGGTCCTTTACCCAATGG
       G  L  P  G  E  K  G  H  P  G  P  P  G  L  P  G  N  G  L  P

1981 AGGACTTCCTGGACCCCGTGGGCTTCCTGGAGATAAAGGCAAGGATGGATTACCGGGACA
     ----+----+----+----+----+----+----+----+----+----+----+----+  2040
     TCCTGAAGGACCTGGGGCACCCGAAGGACCTCTATTTCCGTTCCTACCTAATGCCCTGT
       G  L  P  G  P  R  G  L  P  G  D  K  G  K  D  G  L  P  G  Q

2041 ACAAGGCCTTCCCGGATCTAAGGAATCACCCCTGCTAGTTATTCCTGGTCATACGG
     ----+----+----+----+----+----+----+----+----+----+----+----+  2100
     TGTTCCGGAAGGGCCTAGATTCCCTTAGTGGACGGGACATAATAAGGACCCAGTATGCC
       Q  G  L  P  G  S  K  G  I  T  L  P  C  I  I  P  G  S  Y  G

2101 TCCATCAGGATTCCCAGGCCTGAGGGCCTAAGGTCCGGATTCCCAGGCTCCGAGGCCTCCC
     ----+----+----+----+----+----+----+----+----+----+----+----+  2160
     AGGTAGTCCTAAGGTCCGGACTCCCGGATTCCAGGCCTAAGGGTCCGAGGCTCCGGAGG
       P  S  G  F  P  G  T  P  G  F  P  G  P  K  G  S  R  G  L  P
     TGGGACCCCAGGCCAGCCTGGTCAAGTGGAAGTAAGGAGAGCCAGGAGTCCAGGATT
```

FIG. 1H

```
2161  ACCCTGGGTCCGGTCGGACCCAGTTCACCTTCATTCCTCTCGTCCTCAGTCCTAA  2220
          G  T  P  G  Q  P  G  S  S  K  G  E  P  G  S  P  G  L

2221  GGTTCATCTTCCTGAATTACCAGGATTTCCTGGGGAGAAGGGCTTGCCTGG  2280
          V  H  L  P  E  L  P  G  F  P  G  P  R  G  E  K  G  L  P  G

2281  CCAAGTAGAAGGACTTAATGTCCTAAAGGACCTGGAGCACCCTCTTCCCGAACGGACC  2340
          F  P  G  L  P  G  K  D  G  L  P  G  M  I  G  S  P  G  L  P

2341  GTTCCTGGGCTCCCTGGAAAAAGATGATTGCCTGGATGGCAGTCCAGGCTTACC  2400
          G  S  K  G  A  T  G  D  I  F  G  A  E  N  G  A  P  G  E  Q

2401  CAAAGGACCCGAGGACCTTTCTACCGAACGGTCCAGTCCAGTCCGAATGG  2460
          G  L  Q  G  L  T  G  R  K  G  F  L  G  D  S  G  L  P  G  L

2461  TGGTTCCAAGGAGGAGCCACTGGTGACATCTTGGTGCTGAAAATGGTGCTCCGGGGAACA  2520
```

```
                ACCAAGGTTCCTCCGGTGACCACTGTAGAAACCACGACTTTACCACGAGGCCCCTTGT
                AGGCCTACAAGGATTAACAGGGCACAAAGGATTTCTGGAGACTCTGGCCTTCCAGAGACT

TCCGGATGTCCTAATTGTCCCGTGTTCCTAAAGAACCTCTGAGACCGGAAGTCCTGA

CAAGGGTGTGCACGGGAAGCCTGGCTTACTAGGCCCAAAGGTGAGCGGCAGCCCTGG
                GTTCCCACACGTGCCCTTCGGACCGAATGATCCGGGTTTCCACTCGCCCCGTGCGGACC
```

FIG. 11

```
       K  G  V  H  G  K  P  G  L  L  G  P  K  G  E  R  G  S  P  G
2521   GACACCAGGACACAGGTGGGACAGCACCCCAGGACTTAGTGGTCCATATGGCATCAA    2580
       CTGTGGTCCTGTGTCCACCCTGTCGTTCCGGGGTCCTAGATCACCAGGTATACCGTAGTT
       T  P  G  Q  Q  P  G  T  P  G  S  S  G  P  Y  G  I  K
       GGGCAAATCTGGGCTCCCAGGAGCCTTCCCAGGCATCTCAGGACATCCTGGAAA        2640
2581   CCCGTTTAGACCCGAGGGTCCTCGTGTCCGAAGGGTCCTAGAGTCCTGTAGGACCTTT
       G  K  S  G  L  P  G  A  P  G  F  P  G  I  S  G  H  P  G  K
       GAAAGGAACAAGAGGCAAGAAAGGTCCTCCTGATCAATTGTAAAGAAAGGCTGCCAGG    2700
2641   CTTTCCTTGTTCTCCGTTCTTTCCAGAGGACCTAGTTAACATTTCTTTCCGACGGTCC
       K  G  T  R  G  K  K  G  P  P  G  S  I  V  K  K  G  L  P  G
       GCTAAAAGGCCTTCCTGGAAATCCAGGCCTAGTAGGACTGAAAGGAAGCCCAGGCTCTCC  2760
2701   CGATTTTCCGGAAGGACCTTTAGGTCCGGATCATCCTGACTTTCCTTCGGGTCCGAGAGG
       L  K  G  L  P  G  N  P  G  L  V  G  L  K  G  S  P  G  S  P
       AGGGGTCGCTGGGTTGCCTGCAGCCCTCTCTGACCCCCAAGGAGAGAAGGGTCTGTTGGATT 2820
2761   TCCCCAGCGACCCAACGGTCGGGAGACCTGGTTCCTCCTCTTCCCCAGACAACCTAA
       G  V  A  G  L  P  A  L  S  G  P  K  G  E  K  G  S  V  G  F
```

FIG. 1J

```
2821  CGTAGGTTTTCCAGGAATACCAGGTCCTGCCTGTATCCTGGAACAAGAGGATTAAAAGG
      ------+---------+---------+---------+---------+---------+  2880
      GCATCCAAAAGGTCCTTATGGTCCAGGACGGACCATAAGGACCTTGTTCTCCTAATTTTCC
       V  G  F  P  G  I  P  G  L  P  G  T  R  G  L  K  G

2881  AATTCCAGGATCAACTGGAAAATGGGACCATCTGGACGCGGTGTACTCCTGTGAAAA
      ------+---------+---------+---------+---------+---------+  2940
      TTAAGGTCCTAGTTGACCTTTTACCCTGGTAGACCTGCGCCACATGAGGACACTTTT
       I  P  G  S  T  G  K  M  G  P  S  G  R  A  G  T  P  G  E  K

2941  GGGAGACAGAGGCAATCCGGGGCCAGTCGGAATACCTAGTCCAAGACGTCCAATGTCAAA
      ------+---------+---------+---------+---------+---------+  3000
      CCCTCTGTCCTCCGTTAGGCCCCGGTCAGCCTTATGGATCAGGTTCTGCAGTTACAGTTT
       G  D  R  G  N  P  G  P  V  G  I  P  S  P  R  R  P  M  S  N

3001  CCTTTGGCTCAAGGAGACAAAGGAGGAGCTGTGTACCAGGTCCTAGGTTACCTAAAGGACC
      ------+---------+---------+---------+---------+---------+  3060
      GGAAACCGAGTTCCTCTGTTTCCTCTTCGACACATGGTCCAGATCCAATGGATTCCTGG
       L  W  L  K  G  D  K  G  S  Q  G  S  A  G  S  N  G  F  P  G

3061  GCCAAGAGGTGACAAAGGAGGAGGCTGTGTCCGACCAGGCCTGGACCTGGAGCTCC
      ------+---------+---------+---------+---------+---------+  3120
      CGGTTCTCCACTGTTGTTCCTCTCCGACCAGGCTGTGGTCCGGATGGACCTCGAGG
       P  R  D  K  G  E  A  G  R  P  G  P  P  G  L  P  G  A  P
      TGGCCCTCCCAGGCATTATCAAAGGAGTTAGTGTGAAAGCCAGGGCCCCCTGGCTTCATGGG
```

FIG. 1K

```
3121  ACCGGAGGGTCCGTAATAGTTCCTCAATCACCTTTCGGTCCCGGGGACCGAAGTACCC  3180
      ----------+---------+---------+---------+---------+---------+
      TGGCCTCCCAGGCATTATCAAGGAGTTAGTGGAAAGCCAGGGCCCCTGGCTTCATGGG
       G  L  P  G  I  I  K  G  V  S  G  K  P  G  P  P  G  F  M  G

3181  AATCCGGGGTTACCTGGCCTGAAAGGGTCCTCTGGGATCACAGGGTTCCCAGGAATGCC  3240
      ----------+---------+---------+---------+---------+---------+
      TTAGGCCCCAATGGACCGGACTTCCCAGGAGACCCTAGTGTCCAAAGGGTCCTTACGG
       I  R  G  L  P  G  L  K  G  S  S  G  I  T  G  F  P  G  M  P

3241  AGGAGAAAGTGGTTCACAAGGTATCAGAGGGTCGCCTGGACTCCCAGGAGCATCTGGTCT  3300
      ----------+---------+---------+---------+---------+---------+
      TCCTCTTTCACCAAGTGTTCCATAGTCTCCCAGCGGACCTGAGGGTCCTCGTAGACCAGA
       G  E  S  G  Q  I  R  G  S  P  G  L  P  G  A  S  G  L

3301  CCCAGGCCTGAAAGGACAACGGCCAGACAGTGAATTCCGTAGCCCAGGACCCAA  3360
      ----------+---------+---------+---------+---------+---------+
      GGGTCCGGACTTTCCTGTTGCCGGTCTGTCAACTTAAAGGCATCGGGTCCTGGGTT
       P  Q  A  L  K  D  N  G  Q  T  V  E  I  S  G  P  P  K

3361  GGGACAGCCTGGCGAATCTGGTTTTAAAGGCACAAAGGAAGATGGACTAATAGGCAA  3420
      ----------+---------+---------+---------+---------+---------+
      CCCTGTCGGACCGCTTAGACCAAAATTTCCGTGTTTCCTTCTACCTGATTATCCGTT
       G  Q  P  G  E  S  G  F  K  G  T  K  G  R  D  G  L  I  G  N

3421  TATAGGCTTCCCTGGAAACAAAGGTGAAATGGAAAGTTGGTGTTTCTGGAGATGTTGG  3480
      ----------+---------+---------+---------+---------+---------+
      ATATCCGAAGGGACCTTTGTTTCCACTTCTACCTTTCAACCACAAAGACCTCTACAACC
```

FIG. 1L

```
3481  I  G  F  P  G  N  K  G  E  D  G  K  V  G  V  S  G  D  V  G
      CCTTCCTGGAGCTCCAGGATTCCAGAGTTGCCGGATGAGAGAACCAGGACTTCC   3540
      ----+----+----+----+----+----+----+----+----+----+----+
      GGAAGGACCTCGAGGTCCTAAAGGTCCTCAACGGCCTACTCTCCTTGGTCCTGAAGG
         L  P  G  A  P  G  F  P  G  V  A  G  M  R  G  E  P  G  L  P

3541  AGGTTCTTCTGGTCACCAAgGGGCAATTGGGCCTCTAGGATCCCCCGATTAATAGGACC  3600
      ----+----+----+----+----+----+----+----+----+----+----+
      TCCAAGAAGACCAGTGGTTCCCCGTTAACCCGGAGATCCTAGGGGGCCTAATTATCCTGG
         G  S  S  H  Q  G  A  I  G  P  L  G  S  P  G  L  I  G  P

3601  CAAAGGCTTCCCTGGATTTCCTGGTTACATGGACTGAATGGCTTCCGGGCACCAAGGG   3660
      ----+----+----+----+----+----+----+----+----+----+----+
      GTTCCGAAGGGACCTAAAGGACCAATGTACCTGACTTACCCGAAGGCCCGTGGTTCCC
         K  G  F  P  G  F  P  G  L  H  G  L  N  G  L  P  G  T  K  G

3661  TACCCATGGCACTCCAGGACCTAGTATCATAGTGGCCACACGGACCGGACCAGAGGGACC  3720
      ----+----+----+----+----+----+----+----+----+----+----+
      ATGGGTACCGTGAGGTCCTGGATCATAGTATCACCGGTGTGCCTGGCCTGGTCTCCCCTGG
         T  H  G  T  P  G  P  S  I  T  G  V  P  G  P  A  G  L  P  G

3721  ACCCAAAGGAGAAAAAGGATATCCAGGAATTGGCATCGGAGCTCCAGGAAGCCCGGGCCT  3780
      ----+----+----+----+----+----+----+----+----+----+----+
      TGGGTTTCCTCTTTTTCCTATAGGTCCTTAACCGTAGCCTCGAGGTCCCTTCGGCCCGGA
         P  K  G  E  K  G  Y  P  G  I  G  I  G  A  P  G  K  P  G  L
```

FIG. 1M

```
3781  GAGAGGGCAAAAGGTGATCGAGGTTCCCAGGCCCTGCTGGTCTCCCGG   3840
      ----+----+----+----+----+----+----+----+----+----+
      CTCTCCCGTTTTCCACTAGCTCCAAGGGTCCGGGACGACCAGAGGGCC
      R  G  Q  K  G  D  R  G  F  P  G  L  Q  G  P  A  G  L  P  G

3841  TGCCCCAGGCATCTCCTTGCCCTCACTCATAGCAGGACAGCCTGGTGACCCCGGCGACC   3900
      ----+----+----+----+----+----+----+----+----+----+
      ACGGGGTCCGTAGAGGAACGGGAGTGAGTATCGTCCTGTCGGACCACTGGGGCCGCTGG
      A  P  G  I  S  L  P  S  L  I  A  G  Q  P  G  D  P  G  R  P

3901  AGGCCTAGAGATGGAGAACGAGGCCCCAGGCCCCGCTGGACCCCCAGTCCCCCTGGGCC   3960
      ----+----+----+----+----+----+----+----+----+----+
      TCCGGATCTACCTCTTGCTCCGGGGTCCGGGGCGACCTGGGGGTCAGGGGGACCCGG
      G  L  D  G  E  R  G  R  P  G  P  A  G  P  P  G  P  P  G  P

3961  ATCCTCGAATCAAGGAGACCAAGGAATTCCAGTTTTTCTGGCCTCCCTGGAGAGCTGGATTCC   4020
      ----+----+----+----+----+----+----+----+----+----+
      TAGGAGCTTAGTTCCTCTGGTTCCTTAAGGTCAAAAGACCGGAGGACCTCTCGATCCTAAGG
      S  S  N  Q  G  D  T  D  P  G  F  P  G  I  P  G  P  K  G

4021  CGGATTCCCTCTGTTCCTCTGGCCCTCCCAAGGTGACCTCGATCCTGACTT   4080
      ----+----+----+----+----+----+----+----+----+----+
      GCCTAAGGGAGACAAGGAGACCAAGGAGTCCAAAAGACCGGAGGACTAGGACTGAA
      P  K  G  D  Q  G  I  P  G  F  S  G  L  P  G  E  L  G  L  K

AGGCTCTCTGGCCCTCCAAGGTGATCCTCGACAAACACCAACTGCAGAAGCTGTCCAGT
```

FIG. 1N

```
4081  ------------------------------------------------------------  4140
      TCCGAGAAGACCGGAGGTTCCACTAGGACCTGTTTGTGGTTGACGTCTTCGACAGTCCA
      AGGCTCTTCTGGCCTCCAAGGTGATCCTGGACAAACACCAACTGCAGAAGCTGTCAGGT
       G  S  S  G  L  Q  G  D  P  G  Q  T  P  T  A  E  A  V  Q  V

4141  ------------------------------------------------------------  4200
      TCTCCTGGACCCTTGGGTCTCTACCAGGATCGATGGACCTAGGACCGGAGTGACCCTGGG
      AGGAGGACCTGGGAACCCAGAGATGGTCCTAGCTACCTGGATCCTGGCCTCACTGGGACC
       P  P  G  P  L  G  L  P  G  I  D  G  I  P  G  L  T  G  D  P

4201  ------------------------------------------------------------  4260
      TGGGGCTCAAGGCCCTGTAGGCCTACAAGGCTCCAAAGGTTTACCTGGCATCCCCGGTAA
      ACCCCGAGTTCCGGGACATCCGGATGTTCCGAGGTTTCCAAATGGACCGTAGGGGCCATT
       G  A  Q  G  P  V  G  L  Q  G  S  K  G  L  P  G  I  P  G  K

4261  ------------------------------------------------------------  4320
      AGATGTGTCCCAGTGGGCCCCAGGCTCTTGTTGGTGATCCTGGTGTCCTGCCTGG
      TCTACACAGGGTCACCCGGAGGGTCCGAGAACAACCACTAGGACCACAGACGGACC
       D  G  P  S  G  L  P  G  P  P  G  A  L  G  D  P  G  L  P  G

4321  ------------------------------------------------------------  4380
      ACTGCAAGGCCCTCCAGGATTGAAGAGCTCCGAGTCCCGTTCCGGAAGCCCTACGGA
      TGACGTTCCGGGAGGTCCTAACTTCTCGAGGCTCAGGGCAAGGCCTTCGGGATGCCT
       L  Q  G  P  P  G  F  E  G  A  P  G  Q  Q  G  P  S  G  L

4381  ------------------------------------------------------------  4440
      GGAATGCCTGGCCAGAGCATGAGAGTGCTACACGTTGGTAAAGCACAGCCAGTCGGAA
      CCTTACGGACCGGTCTCGTACTCTCACCCGATGTGCAACCATTTCGTGTCGGTCAGCCTT
```

FIG. 10

```
       E  C  L  A  R  A  *  E  W  A  T  R  W  *  S  T  A  S  R  N
     CAGGTGCCCCCGTGTCCCATCGGgATGAGCCAGCTGTGGGTGTGGGTACAGCTTACTGTTT
4441 ------+---------+---------+---------+---------+---------+ 4500
     GTCCACGGGGGCACAGGGTAGCCCTACTCGGTCGACACCCCATGTCGAATGACAAA
       R  C  P  R  V  P  S  G  *  A  S  C  G  W  G  T  A  Y  C  L

G  T  G  G  A  G  G  G  G  C  A  A  C  A  A  A  G  C  C  A  C  A  G  G  A  C  C  T  G  G  C  T  T  T  G  C  T  G  C  C  T  C  C  T  G  T  C  T  G  C  C  C
4501 ------+---------+---------+---------+---------+---------+ 4560
     CACCTCCCCGTGTTGTTTCGGGTGTCCTGGACCGAAACGACCGAGGACAGACGGG
       W  R  G  N  T  K  P  T  T  R  T  W  A  L  L  A  P  V  C  P

CGCtTCAGCACCATGCCCTCACTACTGCAACATCAaCGAGGTGCCACTATGCCAGGCG
4561 ------+---------+---------+---------+---------+---------+ 4620
     GCGaAGTCGTGGTACGGGAGTGATGACGTTGTAGTTGCTCCACGGTGATACGGTCCGC
       A  S  A  P  C  P  H  Y  C  N  I  N  E  V  C  H  Y  A  R  R

CAATGATAAATCTTACTGGCTCTCCACTACCGCCCATGATGCCCGTCAGCCA
4621 ------+---------+---------+---------+---------+---------+ 4680
     GTTACTATTTAGAATGACCGAGAGGTGATGGCGGGGATAGGGTACTACGGCAGTCGGT
       N  D  K  S  Y  W  L  S  T  T  A  P  I  P  M  M  P  V  S  Q

GACCCAGATTCCCCAGTACATCAGCCGCTCTGTGTGTGAGGCACCCTCGAAGCCATT
4681 ------+---------+---------+---------+---------+---------+ 4740
     CTGGGTCTAAGGGGTCATGTAGTCGGCGAGACACACACTCCGTGGGAGCTTCGGTAA
       T  Q  I  P  Q  Y  I  S  R  C  S  V  C  E  A  P  S  K  P  F
```

FIG. 1P

```
4741  CTGTGCACAGCCAGGACATCACCATCCCGCAGTGCCCCCTGGGCGCAGCCTCTGGA
      GACACGTGTCGGTCCTGTAGTGGTAGGGCGTCACGGGAACCCGCGTCGGAGACCT
       C  A  Q  P  G  H  H  P  A  V  P  P  G  L  A  Q  P  L  D

4801  TTGGGTACTCTTTCCTCATGCCACACTGCACTGCCGTGTGCCGAGGGTGGAGGCAGTCCCTGGT
      AACCCATGAGAAAGGAGTACGTGTGACGGCGACCACGCGCTCCCACCTCCGTCAGGACCA
       W  V  L  F  P  H  A  H  C  R  W  C  R  G  W  R  Q  S  L  V

4861  CTCACCTGGCTCCCTCCTAGAGACTTTCGGCCCACTCCTTTCATCGAATGCAGTGCCCG
      GAGTGGACCGAGGAGGATCTCCTGAAAGCCGGTGAGGAAGTAGCTTACGTCACCGGGC
       S  P  G  S  S  *  R  T  F  G  P  L  L  S  S  N  A  V  R

AGGCACCTGCCACTACTTTGCAAACAAGTACAGTTTCTGGTTGACCACAGTGGAGGAGAG
```

```
4921 TCCGTGGACGGTGATGAAACGTTTGTTCATGTCAAAGACCAACTGGTGTCACCTCCTC 4980
      G  T  C  H  Y  F  A  N  K  Y  S  F  W  L  T  T  V  E  E  R

4981 GCAGCAGTTTGGGGAGTTGCCTGTGTCTGAAACGCTGAAAGCTGGGCAGCTCCACACTCG 5040
      Q  Q  F  G  E  L  P  V  S  E  T  L  K  A  G  Q  L  H  T  R

5041 CGTCGTCAAACCCCTCAACGGACACAGACTTTGCGACTTTCGACCCGTCGAGGTGTGAGC 5100
      AGTCAGTCGCTGCCAGGTGTGTATGAACCGGAATTCCAGCTGGCCGGTCGCTCCATTC
      S  Q  S  C  Q  V  C  M  N  R  N  S  S  W  R  R  S  L  H  S

```
6   1                                          MLIN
α2  1                              MGRDQRAVAGPA-RR
α1  1                                       MGPRDSV
α5  1                              MKLR       GVS-AA
                                   ▼    ▼   ▼▼
    5   KLWLLLVTLCLTEELAAAGEKSYGKPCGGODCSGSCQCFP
    16  W-L-GT--VGFLAQSVL--V-KFDV----R----G---Y-
    8   W-L--PAA-L-H--HSR-AA-    GG-A-SG- -K-D-HG
    11  G-F--   A-S-WGQP-E-AA    -Y-CSPGSK-D-SG
                                      ▲
    45  EKGARGRPGPIGIQGPTGPQGFTGSTGLSGLKGERGFPGL
    56  ---G--Q---V-P--YN--P-LQ-FP--Q-R--QK-ER-A
    44  V--QK-ER-LP-L--VI-FP-MQ-PE-PQ-PP-QK-DT-E
    43  I--EK-ER-FP-LE-HP-LP--P-PE-PP-PR-QK-DD-I

85  LGPYGPKGDKGPMGVPGFLGINGIPGHPGQPGPRGPPGLD
    96  P-VT-----V-AR--S--P-AD--------G----R--Y-
    84  P-LP-T--TR--P-AS-YP-NP-L--I---D--P----IP
    83  P--P----IR--P-L---P-TP-L--M--HD-AP--Q-IP
        ▼
    125 GCNGTQGAVGFPGFDGYPGLLGPPGLPGQKGSKGDPVLAP
    136 -------DS-PQ--P-SE-FT----PQ-P--Q--E-YAL-
    124 -----K-ER-PL--P-L--FA-N--P--LP-M----GEIL
    123 -----K-ER----SP-F---Q----P--IP-M--E-GSII

165 GSFK    GIKGDPGLPGLDGITGPQGAPGFPGAVGPAGPPG
    176 KEERDRYR -E--E---V-FQ--P-R--HV-QM--V-A--
    164 -HVPGMLL--ER-F--IP-TP--P-L--LQ-P---P-FT-
    163 M-SLP-P  --N--Y--PP--Q-LP-PT-I--PI--P----
                I
    203 LQGFPGPPGPLGPDGNMGLGFQGEKGVKGDVGLPGPAGPP
    215 RP--------K-QQ--R----Y-V--E-----Q---N-I-
    204 PP--------P-EK-Q---S---P--D---Q-VS--P-V-
    202 -M-------LP--K-----N---P--E--EQ-Q--P---
                                II
    243 PSTGELEFMGFPKGKKGSKGEPGPKGFPGISGPPGFP
    256 SD-LHPIIAPTGVTFHPDQYK -E--GE-EP-IR-IS
    244 GQAQVQ-KGD-ATK        -E--QK-EP-FQ-M-
    242 GQIS-QKRPIDVEFQ--DQ-L--DR-P--PP-IR-P-GPP
              III
```

FIG. 3B

```
280 GLGTTGEKGEKGEKGIPGLPGPRGPMGSEGVQGPPGQQGK
292 LK-EE-IM-FP-LR-Y---S-EK-SP-QK-SR-LD-Y--P
273 -V-EK--P-KP-PR-K--KD-DK-EK--P-FP-E--YP-L
282 - -EK-----Q--P-KR-K--KD-EN-QP-IP-L--DP-Y
            IV
320 KGTLGFPGLNGFQGIEGQKGDIGLPGPDVFIDIDGAVISG
332 D-PR-PK-EA-DP-PP-LP         AYSPHPSLAK-
313 I-RQ-PQ-EK-EA-PP-PP-IV      IGTGPLGEKG
321 P-EP-RD-EK-QK-DT-PP-PP--  VIPRPGTGITIGEK-
                                            V
360 NPGDPGVPGLPGLKGDEGIQGLRGPSGVPGLPALSGVPGA
362 AR----F--AQ-EP-SQ-EP-DP-LP-P---SIGD-DQRR
345 ER-Y--T--PR-EP-PK-FP--P-QP-P----VP -QA--
360 -I-L--L--EK-ER-FP----PP-LP-P--AAVM -P--P
                                        VI
400 LGPQGFPGLKGDQGNPGRTTI   GAAGLPGRDGLPGPPGP
402   -LP-EM-P--FI-D--IPALYG-PP-PD-KR-P-----L
384 P-FP-ER-E---R-F--TSLP   -PS-RD-LP-P--S---
399 P-FP-ER-Q---E-P--ISIP   -PP--D-QP-A--L---
                    VII
438 PGPPSPEFETETLHNKESGFPGLRGEQGPKGNLGLKGIKG
441 ----G-DGF LEGLKGAK-PA-FP-LP-SP-AR-PK-W--
422 --Q-GYTNGIVECQPGPP-DQ-PP-IP-QP-FI-EI-E--
437 ---AG-HIPPSDEICEP -P--PP-SP-D--LQ-EQ-V--
         ▼▼     VIII
478 DSGFCACDGGVPNT GPPGEPGPPGPWGLIGLPGLKGARG
480 -A-E-R-TE-DEAIK-L--L---K-FA-IN-E--R--DK-
462 QK-ESCLICDIDGYR----PQ----EI-FP-Q---A--D--
476 -K-DTCFNCIGTGIS----Q--L--LP-PP-SL-FP-QK-
         ▲  ▲   IX
517 DRGSGGAQGPAGAPGLVGPLGPSGPKGKKGG          548
520 -P-QH-LP-FP-LK-VP-NI-AP----A--D          551
502 LP-RD-VA-VP-PQ-TP-LI-QP-A--EP-E          533
516 EK-QA--T--K-L--IP-AP-AP-FP-S--E          547
```

COLLAGEN COL4A6: GENE, PROTEIN AND METHOD OF DETECTING COLLAGEN DEFICIENCY

This application is a continuation of application Ser. No. 08/112,465, filed Aug. 27, 1993 now abandoned.

FIELD OF THE INVENTION

The present invention relates, in general, to a genetic method for detecting collagen deficiencies associated with Alport's syndrome, and to a type IV collagen protein designated α6(IV), and a gene COL4A6.

BACKGROUND OF THE INVENTION

Alport's syndrome ("AS") is disorder characterized by progressive kidney disease (glomerulonephritis), progressive hearing loss (sensorineural deafness) and eye lesions (lenticonus). Alport's syndrome is usually dominantly inherited and occurs in the population at a frequency of about 1/5000 persons, with greater frequency in males. Progressive kidney failure causes death in many AS patients.

Alport's syndrome is a progressive disease, usually inherited as an X-chromosome-linked dominant trait, but autosomal forms have been described. In AS, ultrastructural defects are present in the glomerular basement membrane ("BM"), a complex network of glycoproteins and collagens, which serves an important function in filtration in the kidney.

Recently, mutations in the collagen gene COL4A5, a specific component of the BM within the kidney, were correlated with Alport's syndrome in three kindred patients. Both point mutations and intragenic deletions of COL4A5, which maps to the X chromosome, have been implicated in Alport's syndrome. (See, Barker et al., *Science* 248:1224 (1990); Zhou et al., *Genomics* 8:10 (1991); Antignac et al., *Kidney Int.* 42:1178 (1992)).

In some families, AS cosegregates with the occurrence of diffuse leiomyomatosis ("DL"), a benign proliferation of smooth muscle in the esophagus, female genitalia, and trachea. These benign tumors found in DL are commonly known as fibroids.

Recently, three out of three AS-DL patients were shown to have deletions that include the 5' end of COL4A5. The association of AS and DL in patients raised the possibility that COL4A5 or another gene was exerting pleiotropic effects in causing DL, or that a tumor or suppressor gene might exist in the vicinity upstream of COL4A5. Alternatively, the fact that familial leiomyomatosis, a non-AS linked disorder, occurs with autosomal dominant inheritance (as opposed to X-linked) urged that an unrelated gene was at work. Despite these hypotheses, there exists no coherent understanding in the field of the causative factor(s) behind AS-DL.

SUMMARY OF THE INVENTION

It is therefore an object of the present invention to provide a polynucleotide molecule, COL4A6, encoding α6(IV). Assays according to the invention, employ such a gene and a protein encoded thereby to detect a collagen type IV-associated pathology, preferably Alport's syndrome, and more preferably, AS-DL. These assays are based on (a) structural and sequence evaluation of an α6(IV) gene and (b) evaluation of its expression patterns, either at the DNA, RNA, and/or protein levels.

A further objective is to provide a gene for use in gene therapy of a patient having a collagen type IV-associated pathology, by administering to a patient a vector containing an α6(IV)-encoding polynucleotide molecule such that transfection with the vector induces production of an effective amount of α6(IV) in the patient. Preferably, the collagen type IV-associated pathology is Alport's syndrome, or is a subset of Alport's syndrome, AL-DS.

In accomplishing these and other objects of the invention, in accordance with one aspect of the present invention, an isolated COL4A6 polynucleotide molecule comprising a DNA sequence encoding a α6(IV) polypeptide is provided.

Another object of the invention is to provide a method for detecting a collagen type IV-associated pathology comprising the step of determining the presence or absence of a structural alteration in COL4A6 polynucleotide molecule in a biological sample by comparing said sample COL4A6 with a standard that is indicative of an unaltered COL4A6 polynucleotide molecule.

Another object of the present invention is to provide an isolated α6(IV) collagen polypeptide. An α6(IV) polypeptide provided according to the invention is useful for generating monoclonal or polyclonal antibodies having specificity for α6(IV) polypeptide, preferably an antibody that is not cross-reactive with other collagen proteins, including at least, α1(IV), α2(IV), α3(IV), α4(IV) or α5(IV) collagens.

α6(IV)—specific antibodies, and in particular, labeled monoclonal α6(IV)-specific antibodies, are useful for detection of collagen type IV-associated pathologies.

BRIEF DESCRIPTION OF THE FIGURES

FIGS. 1A–1Q show a COL4A6 polynucleotide molecule (SEQ. ID NO: 1, and below, α6(IV) polypeptide molecule (SEQ ID NO: 2). Within the full-length polynucleotide spanning 5102 nucleotides and the corresponding polypeptide molecule spanning 1700 amino acids, a fragment molecule also is identified spanning amino acids 1–1460 inclusive and nucleotides 1–4380 inclusive, respectively.

FIGS. 3A–3B show deduced amino acid sequences of the cDNA clone JZ-3 of the human α6(IV) chain (SEQ ID NO: 7) and comparison of JZ-3 with the amino acid sequences of the human α1(IV) (SEQ ID NO: 9), α2(IV) (SEQ ID NO: 8) and α5(IV) (SEQ ID NO: 10) chains. Dashes indicate amino acid identity, and conserved cysteine residues are indicated by arrows. The locations of cysteines in the mature chains are identical in α6(IV) and α2(IV). Interruptions in the collagenous repeat are underlined and numbered (I through IX).

DETAILED DESCRIPTION OF THE PREFERRED EMBODIMENTS

Figure 2:
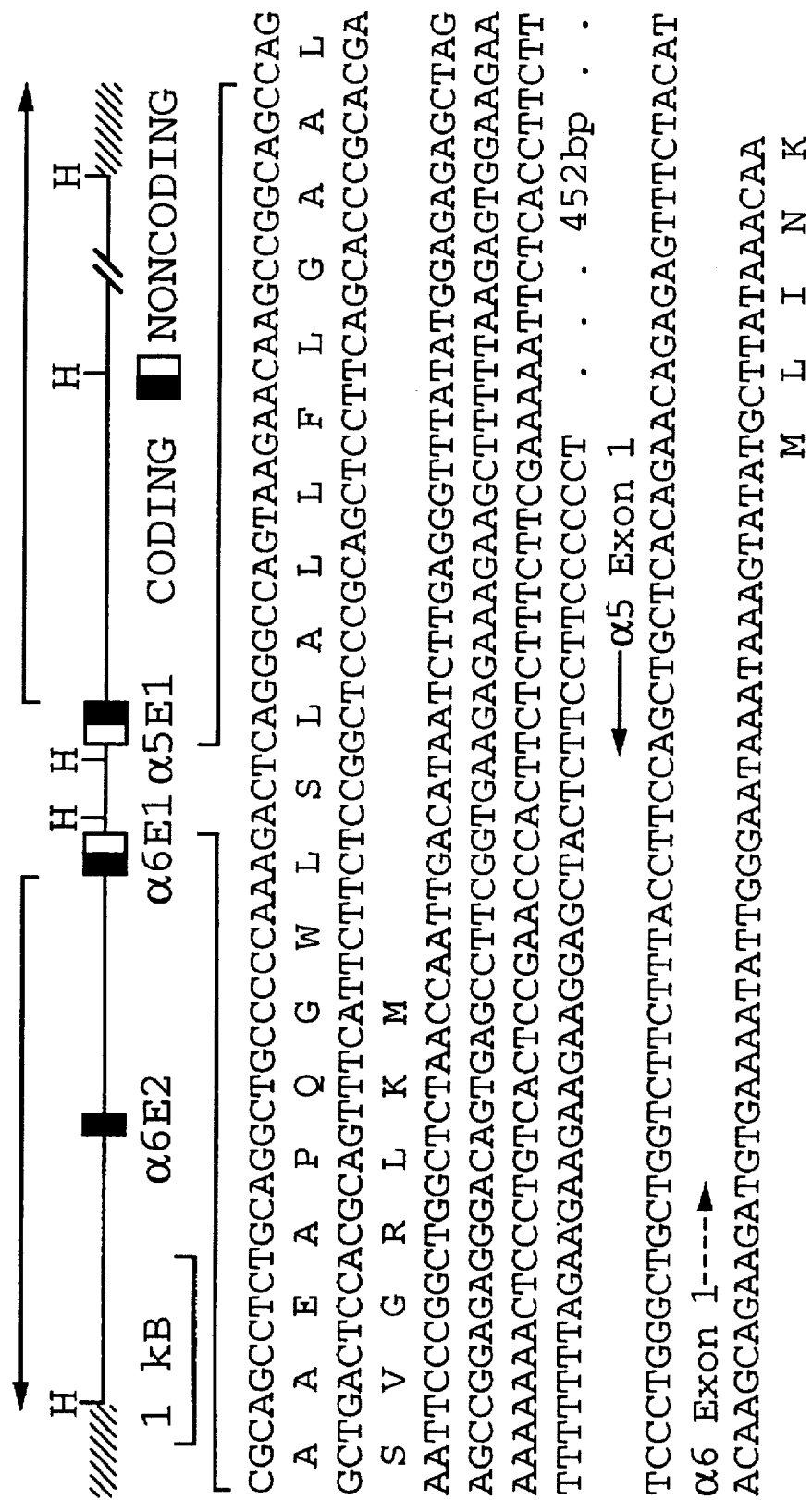
FIG. 2 shows a restriction map of lambdaLA226 which contains the 5' ends of both COL4A6 and COL4A5. The striped bars represent phage arms; H. Hind III. The DNA sequence of the region containing the first exon of each gene (SEQ ID NOS: 3 and 5) is shown as well as the deduced amino acid sequences of the first exons (SEQ ID NOS: 4 and 6).

According to the present invention, a human polynucleotide molecule, COL4A6, and a corresponding human polypeptide, α6(IV), encoded by COL4A6, are disclosed. Human COL4A6 polynucleotide molecule is expressed primarily by cells that synthesize specialized basement membranes of the body, particularly in the kidney glomerulus, inner ear and esophagus. Also, COL4A6 polynucleotide molecule is expressed in heart, skeletal muscle, lung and placenta (term). Type IV collagens, of which is α6(IV) is a member, are ultrastructural proteins found in the BM and are implicated in adhesion and motility of cells during tumor invasion. According to the present invention, importantly, a variety of alterations to the COL4A6 gene are correlated with "collagen type IV-associated pathologies," a term defined to include, but not be limited to, diseases of the BM, such as Alport's syndrome, AS-DL, and formation and proliferation of benign tumors.

Distribution of α6(IV): Northern Blot Analysis

The distribution of the α5(IV) and α6(IV) transcripts were studied in the fetus. An α6(IV) mRNA of ≈7.0 kb was found in meninges and esophagus and was just detectable in fetal choroid plexus and stomach. An ≈7.0 kb transcript of α5(IV) was present in many tissues but was most abundant in choroid plexus, meninges, and esophagus. This distribution is in agreement with the suggestion that interactions between cells and the underlying basement membrane substrate play a vital role in embryonic morphogenesis.

It is believed that, as a result of this role in development, deletions of both COL4A5 and COL4A6, which were found in all four independent AS-DL kindreds, cause AS-DL based on the following mechanism. Signals from BM proteins, transduced by members of the integrin family of cell surface receptors, regulate cell growth and differentiation and influence cell shape by affecting the cytoskeleton. Several BM components interact with integrins and can affect differentiation of epithelial, endothelial, and mesenchymal cells. Type IV collagens contain binding sites within the triple-helical and NCI domains for several cell types including myocytes. In the presence of antibodies to a β integrin, chicken embryo myoblasts continue to replicate, fail to fuse, and have abnormal morphology. Vandenberg et al., *J. Cell Bio.* 13:1475 (1991). Although the cited studies are based on collagen sources rich in the ubiquitous α1(IV) and α2(IV) chains, the data presented herein suggest that the α5(IV) and α6(IV) chains may play similar roles in cell-matrix interactions in tissues involved in the AS-DL syndrome. Likewise, their absence may disrupt normal morphogenesis and lead to uncontrolled proliferation of distorted smooth muscle cells.

AS-DL: A Suggested Relationship Between COL4A6 & COL4A5

Mutations of neither COL4A5 alone nor COL4A6 alone have been observed in AS-DL. It is possible that only the α6(IV) chain is critical for normal smooth muscle differentiation. If so, our failure to observe mutations of COL4A6 alone in AS-DL might merely reflect the small sample size. Linkage studies have shown that X-linked AS mutations are all tightly linked to markers in the Xq22 region where both COL4A5 and COL4A6 are located. COL4A6 is the probably site for the ≈50% of X-linked AS mutations that have not been found in COL4A5. Therefore, the absence of DL in these patients suggest that simultaneous mutation of both COL4A5 and COL4A6 is required for the development of DL.

According to the present invention, structural alterations in a type IV collagen gene, in particular COL4A6 gene, were detected in a subset of patients exhibiting collagen type IV associated pathologies. The experiments below also show that structural alterations in a type IV collagen can result in cell proliferation resulting in benign tumors, for example, such as leiomyomas.

"Structural alterations" include constitutional rearrangements, including deletion(s), duplicate(s), inversion(s) or point mutation(s) and somatic mutations (in tumors) of the coding and/or regulatory regions, that affect a cell's ability to make functional α6(IV). Thus, the term does not include natural polymorphisms which do not affect the cell's ability to make functional α6(IV). One such functional α6(IV), for example, was identified from cells not exhibiting collagen type IV associated pathologies, shown as the full-length polypeptide in FIG. 1 (SEQ ID NO: 2).

"Altered expression" of α6(IV) or α6(IV) RNA (mRNA) includes a decreased expression of α6(IV) or α6(IV) RNA relative to that found in "normal" cells derived from an individual not exhibiting collagen type IV-associated pathologies. For example, altered expression level of α6(IV) or α6(IV) RNA may include a range from one-half to less than one-half of an amount identified as a median standard expression level.

METHODS FOR DETECTING COLLAGEN

Type IV-Associated Pathology

According to the invention, assays are provided to detect a collagen type IV-associated pathology, based on (a) structural and sequence evaluation of α6(IV) gene and (b) evaluation of related expression patterns, at any of the DNA, RNA, and/or protein levels.

For analyzing genomic structural alterations, known methods are applied, such as utilized by Antignac et al., *Kidney Int.* 42:1178 (1992), incorporated herein by reference in its entirety. A α6(IV) polynucleotide molecule is used to screen for alterations by hybridization in the sample. Thereafter, the α6(IV) gene can be analyzed, for example, by Southern blot, polymerase chain reaction sequence identification of cloned material, single strand conformational polymorphism (SSCP), or by DNA sequencing of the locus.

A probe useful in this context is a labeled fragment of α6(IV) gene or preferably an approximately full-length COL4A6 DNA molecule (useful for detection of deletions) which will hybridize to RNA or DNA from normal cells. In addition to a whole gene or fragment thereof, a probe can include a genomic or cDNA clone, an adjacent region, or a regulatory region of the α6(IV) gene. Such a marker may be labeled by a standard method, such as radiolabelling.

For example, detection is performed first by extracting DNA from peripheral blood leukocytes using standard procedures. Next, DNA digestion is performed using a variety of restriction endonucleases and the resulting fragments are run on gel electrophoresis, followed by transfer to a suitable nylon filter or other support matrix for hybridization. Next, hybridization with a radiolabelled cDNA of COL4A6 polynucleotide molecule, preferably spanning the entire polynucleotide molecule of FIG. 1 (SEQ ID NO: 1) or preferably, nucleotides 1–4380 of FIG. 1, is performed.

Hybridization is performed under stringent conditions (for example, 10% dextran sulfate, 1M NaCl, 10% SDS and 100 µg/ml of sonicated denatured salmon sperm DNA, at a temperature of 42° C. Fragments hybridizing to the genomic marker are isolated and subcloned for sequencing using conventional methods. Nucleotide sequencing is performed, e.g. by dideoxy termination method using universal and sequence-specific primers. The reaction products are analyzed by commercially available automated DNA sequencer.

The resulting sequence information then is analyzed for structural alterations, such as deletions and point mutations in coding and/or regulatory sequences.

RNA ("Northern") blotting is employed, for example, using a COL4A6 polynucleotide molecule of the invention. According to this method, RNA is isolated from tissue by any of a number of standard procedures (Lehrach, H., *Biochemistry*, 16: 4743 (1975)). RNA is subjected to denaturing gel electrophoresis, followed by transfer to nitrocellulose or other support matrix. The COL4A6 mRNA can be detected by hybridization of radioactively or nonradioactively labelled COL4A6, or COL4A6 fragments, preferably under high stringency conditions, such as recognized by a scientist in this field. The amount of hybridization can be quantified by densitometric methods.

In yet another embodiment of the present invention, the polymerase chain reaction ("PCR") is used to detect α6(IV) DNA or RNA in a sample. For example, a pair of COL4A6 sequence specific primers is employed, which hybridize to opposite strands of the α6(IV) gene at offset positions on the double helix. Such primers, taken from the COL4A6 polynucleotide sequences provided in accordance with the invention, represent fragments which preferably are unique to α6(IV), e.g., sequences having low homology with other proteins than α6(IV).

Primers provide initiation points for DNA synthesis. In the presence of DNA polymerase, the four nucleotide triphosphates ("NTPs") and other necessary co-factors, all of which are well known to the art, new DNA strands are synthesized complementary to the templates which hybridized with the primers. Several rounds of synthesis are carried out, with allowance for denaturation of the double-stranded products between rounds. Preferably, a thermal stable DNA polymerase is used so that it is not necessary to add enzyme anew for each round of synthesis.

The PCR produces a double stranded DNA amplification product which has the same sequence as the original stretch of the DNA defined by the ends of the primer pair sequences. PCR can be modified such that it quanitates the amount of α6(IV) DNA or RNA in the sample. See, for example, U.S. Pat. No. 5,219,727. The product can be detected by a variety of methods well-known in the art. Where such products are produced in a test tube, or the like, they can be resolved by agarose or polyacrylamide electrophoresis and detected by fluorescence staining, such as ethidium bromide. Alternatively, one of the NTPs may be labelled and the PCR products may be determined by measuring incorporation of the labeled NTP. A variety of other methods for resolving, detecting and measuring the amount of PCR product are well-known to the art that are suitable for use in the present invention.

PCR may be rendered specific for DNA or RNA in situ and in liquid PCRs. For instance, RNAse or DNAse may be used to remove one template or the other from the sample, and the use of primers that distinguish between the gene and the message, for example, a primer that hybridizes to a sequence in the untranscribed region of the α6(IV) promoter will be gene specific.

Other techniques suitable to the claimed methods are readily apparent to the skilled artisan and can include Nuclease Protection Assays, ELISA and Western blotting. Several assay techniques which are based upon immunological reactions between antigens and antibodies are contemplated by the invention, as well. In particular, assays which use antibodies having specificity for α6(IV) protein are useful to detect cells which produce α6(IV) protein.

The full sequence cDNA shown in FIG. 1 (SEQ ID NO: 1) also allows production of the α6(IV) polypeptide via known recombinant DNA techniques. Recombinant production methods will allow the polypeptide to be obtained in a purified, isolated form, which will permit further study of the α6(IV) polypeptide structure and function. It is further envisioned that such protein production could be scaled up for making large quantities of α6(IV) polypeptide for commercial purposes. α6(IV) polypeptide can be incorporated in drug delivery devices or wound dressings, such as used in surgical applications and burn treatment.

Anti-α6(IV) Antibodies

Antibodies having specificity for α6(IV)—expressing cells are obtained by stimulating the immune system of an animal with α6(IV) protein. In this context, the term "antibody" encompasses monoclonal and polyclonal antibodies. Such an antibody can belong to any antibody class (IgG, IgM, IgA, etc.). According to the present invention, an entire α6(IV) polypeptide is injected into an animal for the purpose of obtaining polyclonal antibodies, or for obtaining lymphocytes or spleen cells for production of monoclonal antibodies.

The general techniques of monoclonal antibody (Mab) production, such as described by Kohler and Milstein, *Nature* 256:495 (1975), are applied to produce a monoclonal antibody having specificity for α6(IV) protein. This procedure includes the steps of isolating lymphocytes of an animal which has been sensitized or injected with α6(IV) polypeptide, fusing them with myeloma cells to produce hybridomas, then screening the hybridomas for production of "anti-α6(IV) antibodies" which bind preferentially to or exhibit binding specificity for α6(IV) polypeptide. Preferably such an antibody is screened to eliminate those antibodies that are cross reactive with other collagen types, such as α1(IV) or α5(IV). Either the full length polypeptide molecule shown in FIG. 1 (SEQ. ID NO: 2), or a fragment such as a fragment spanning amino acids 1–1460, inclusive are used to sensitize the animal.

"Antibody" also encompasses fragments, like Fab and F(ab')₂, of anti-α6(IV) antibodies, and conjugates of such fragments, and so-called "antigen binding proteins" (single-chain antibodies) which are based on anti-α6(IV) antibodies, in accordance, for example, with U.S. Pat. No. 4,704,692, the contents of which are hereby incorporated by reference. Alternatively, Mabs or a fragment thereof within the present invention can be produced using conventional procedures via the expression of isolated DNA which codes for variable regions of such an Mab in host cells like *E. coli*, see, e.g., Ward et al., *Nature* 341:544–546 (1989), or transfected murine myeloma cells. See Verhoyen et al., *BioAssays* 8:74 (1988); Gillies et al., *Biotechnol.* 7:799–804 (1989); Nakatani et al., *Biotechnol.* 7:805–10 (1989).

Assays in which the above antibodies are employed can include enzyme-linked immunosorbent assay (ELISA), radioimmunoassays, immunoelectrophoresis, and the like. Also useful diagnostically are immunohistochemical techniques which employ monoclonal antibodies of known, specific reactivities.

Diagnostic applications of these antibodies are exemplified, according to the present invention, by the use of a kit containing an anti-α6(IV) antibody, which undergoes a reaction with a biological sample to detect α6(IV) protein expression. Such a reaction involves the binding of anti-α6 (IV) antibody to α6(IV) antigen, under conditions permissive of binding. The observation of an antibody-antigen complex in a biological sample indicates a positive result. A kit of this sort could be used to detect the extent of expression of α6(IV) in a particular biological sample from an individual, animal, or cell line.

Such an immunodiagnostic kit can include anti-α6(IV) antibody and a receptacle for containing the antibody in a sterilized form. The kit can further include anti-isotype serum antibody which recognizes the anti-α6(IV) antibody (Fc portion) and which is conjugated to a label, such as an enzyme or fluorescent moiety.

Another embodiment of the present invention concerns gene therapy applications of the human COL4A6 polynucleotide molecule to treat a patient having a collagen type IV-associated pathology. An adenoviral vector or other suitable vector containing a copy of COL4A6 polynucleotide molecule, for example, provides one means for ex vivo gene transfer in the clinical setting. A preferred vector is characterized by its ability to stably integrate into at least the targeted collagen producing cells and to induce production of an effective amount of α6(IV) in such cells of the patient.

A method for gene therapy includes the step of administering to a patient a vector containing human COL4A6 polynucleotide molecule such that transfection with the vector induces production of an effective amount of α6(IV) in the patient.

The present invention is further described with reference to the following, illustrative examples. Unless defined otherwise, all technical and scientific terms used herein have the same meaning as commonly understood by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies known to the art. The materials, methods and examples are illustrative only and not limiting.

EXAMPLE 1

Identification of COL4A6 Polynucleotide and Polypeptide Molecules

To isolate COL4A6, an X-chromosome library was screened with JZ-4, an α5(IV) cDNA clone obtained according to the method of Zhou et al., *J. Biol. Chem.* 267:12475 (1992). [This reference is incorporated by reference in its entirety] A 14.1-kb clone, 2LA226, was isolated, as shown in FIG. 2 (SEQ ID NOS: 3–6). This clone contained exon 1 of COL4A5 and an upstream 2.8-kb Hind III fragment, lambda-LA226-H6, that displayed cross-species hybridization with mouse or cow DNA.

Next, lambda-LA226-H6 was used to probe an adult kidney cDNA library. Three identical clones, JZK-1, JZK-2, and JZ-3, each contained an open reading frame (1643 bp) encoding a 21-amino acid signal peptide, a 25-amino acid noncollagenous segment, and a 502-amino acid collagenous domain with nine interruptions (see FIG. 3) that are believed to confer flexibility in type IV collagens.

The deduced translation product, termed α6(IV), is a type IV collagen that has not previously been detected genetically or biochemically. Sequence analysis clearly places α6(IV) in the α2(IV)-like class (FIG. 3, SEQ ID NOS 7–10).

EXAMPLE 2

A comparison between Unaltered and AS-DL COL4A6 Gene Expression

In normal adult kidney, COL4A6 is expressed, making this collagen gene a good candidate for a second X-linked AS gene. The first known of such genes, COL4A5, harbors mutations in relatively low frequency in AS patients, supporting the likelihood that some other factor, now identified as COL4A6, participates in the X-linked disease. This possibility was confirmed by Southern (DNA) blot analysis 140 AS patients, including four unrelated AS-DL patients (13), with JZ-3. Genomic DNA samples (≈5 µg) from patients and controls were digested with Eco RI and hybridized with JZ-3-FR5, a cDNA fragment containing the first four exons of α6(IV).

Figure 4:
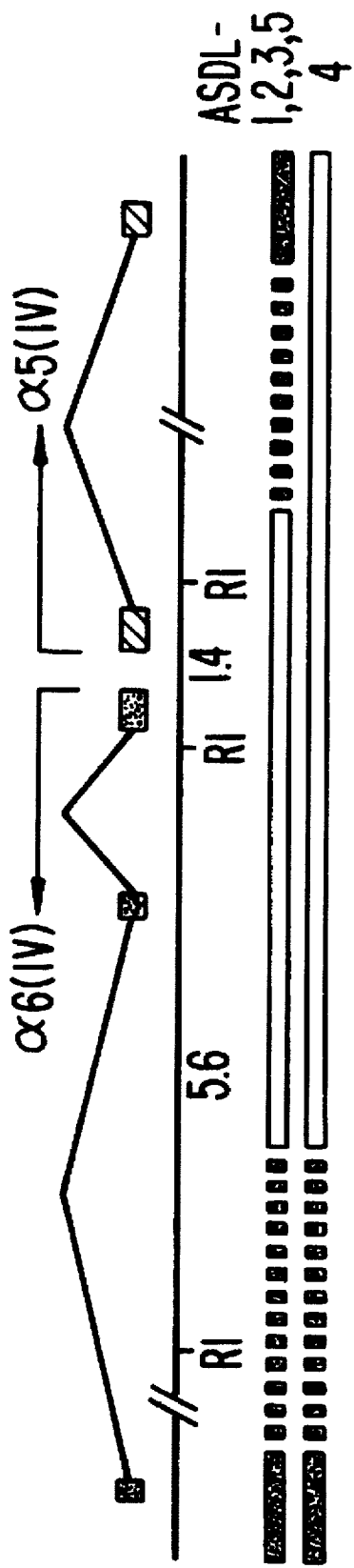
FIG. 4 shows an analysis of collagen gene deletions in five patients with AS-DL of Example 2. The three exons of α6(IV) and two exons of α5(IV) shown as black and striped boxes, respectively, are placed on a genomic map of Eco RI sites (RI). The open bars below show the minimum extent of the deletion in each AS-DL patient. The filed bars show the minimum extent of the nondeleted regions. The shaded bars represent ambiguities in mapping the deletion boundaries.

Analysis of collagen gene deletions in five patients with AS-DL revealed an abnormal pattern in the AS-DL patients, shown in FIG. 4. There was a loss of bands in males and a 50% reduction in the intensity of some bands in females, but the pattern was complex. A fragment containing exons 1 to 4 of COL4A6, JZ-3-FR5, was used to map the deletions more precisely. The 1.4-kb and 5.6-kb Eco RI fragments, which contain exons 1 and 2 of COL4A6, were absent in males and reduced in intensity by ≈50% in females; exons 3 and 4 were intact. Hybridization with JZ-4 demonstrated the loss of exon 1 of COL4A5. Exons 2 to 10 of COL4A5 were present in four of the five patients. Therefore, the smallest AS-DL deletions involve part of intron 1 and all of exon 1 of COL4A5, the intergenetic region, and exons 1 and 2 and part of intron 2 of COL4A6.

---

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 5102 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: join(2..82, 86..97, 101..4399, 4403..4420, 4424
        . . 4465, 4469..4876, 4880..5101)

( x i ) SEQUENCE DESCRIPTION: SEQ ID NO:1:

```
A  ATT  CCG  GTC  CCT  GGG  CTG  CTG  GTC  TTC  TTT  ACC  TTC  CAG  CTG  CTC         46
   Ile  Pro  Val  Pro  Gly  Leu  Leu  Val  Phe  Phe  Thr  Phe  Gln  Leu  Leu
   1         5                        10                       15
```

| | | | | | | | | | | | | | | | | |
|---|---|---|---|---|---|---|---|---|---|---|---|---|---|---|---|---|
| ACA | GAA | CAG | AGA | GTT | TCT | ACA | TAC | AAG | CAG | AAG | ATG | TGA | AAA | TAT | TGG | 94 |
| Thr | Glu | Gln | Arg | Val | Ser | Thr | Tyr | Lys | Gln | Lys | Met | | Lys | Tyr | Trp | |
| | | | 20 | | | | | 25 | | | | | | | 30 | |
| GAA | TAA | ATA | AAG | TAT | ATG | CTT | ATA | AAC | AAG | TTG | TGG | CTG | CTC | CTG | GTT | 142 |
| Glu | | Ile | Lys | Tyr | Met | Leu | Ile | Asn | Lys | Leu | Trp | Leu | Leu | Leu | Val | |
| | | | | | 35 | | | | | 40 | | | | | 45 | |
| ACG | TTG | TGC | CTG | ACC | GAG | GAA | CTG | GCA | GCA | GCG | GGA | GAG | AAG | TCT | TAT | 190 |
| Thr | Leu | Cys | Leu | Thr | Glu | Glu | Leu | Ala | Ala | Ala | Gly | Glu | Lys | Ser | Tyr | |
| | | | | 50 | | | | | 55 | | | | | 60 | | |
| GGA | AAG | CCA | TGT | GGG | GGC | CAG | GAC | TGC | AGT | GGG | AGC | TGT | CAG | TGT | TTT | 238 |
| Gly | Lys | Pro | Cys | Gly | Gly | Gln | Asp | Cys | Ser | Gly | Ser | Cys | Gln | Cys | Phe | |
| | | | 65 | | | | | 70 | | | | | 75 | | | |
| CCT | GAG | AAA | GGA | GCG | AGA | GGA | CGA | CCT | GGA | CCA | ATT | GGA | ATT | CAA | GGC | 286 |
| Pro | Glu | Lys | Gly | Ala | Arg | Gly | Arg | Pro | Gly | Pro | Ile | Gly | Ile | Gln | Gly | |
| | | 80 | | | | | 85 | | | | | 90 | | | | |
| CCA | ACA | GGT | CCT | CAA | GGA | TTC | ACT | GGC | TCT | ACT | GGT | TTA | TCG | GGA | TTG | 334 |
| Pro | Thr | Gly | Pro | Gln | Gly | Phe | Thr | Gly | Ser | Thr | Gly | Leu | Ser | Gly | Leu | |
| | | 95 | | | | | 100 | | | | | 105 | | | | |
| AAA | GGA | GAA | AGG | GGT | TTC | CCA | GGC | CTT | CTG | GGA | CCT | TAT | GGA | CCA | AAA | 382 |
| Lys | Gly | Glu | Arg | Gly | Phe | Pro | Gly | Leu | Leu | Gly | Pro | Tyr | Gly | Pro | Lys | |
| 110 | | | | | 115 | | | | | 120 | | | | | 125 | |
| GGA | GAT | AAG | GGT | CCC | ATG | GGA | GTT | CCT | GGC | TTT | CTT | GGC | ATC | AAT | GGG | 430 |
| Gly | Asp | Lys | Gly | Pro | Met | Gly | Val | Pro | Gly | Phe | Leu | Gly | Ile | Asn | Gly | |
| | | | | 130 | | | | | 135 | | | | | 140 | | |
| ATT | CCG | GGC | CAC | CCT | GGA | CAA | CCA | GGC | CCC | AGA | GGC | CCA | CCT | GGT | CTG | 478 |
| Ile | Pro | Gly | His | Pro | Gly | Gln | Pro | Gly | Pro | Arg | Gly | Pro | Pro | Gly | Leu | |
| | | | 145 | | | | | 150 | | | | | 155 | | | |
| GAT | GGC | TGT | AAT | GGA | ACT | CAA | GGA | GCT | GTT | GGA | TTT | CCA | GGC | CCT | GAT | 526 |
| Asp | Gly | Cys | Asn | Gly | Thr | Gln | Gly | Ala | Val | Gly | Phe | Pro | Gly | Pro | Asp | |
| | | | 160 | | | | | 165 | | | | | 170 | | | |
| GGC | TAT | CCT | GGG | CTT | CTC | GGA | CCA | CCC | GGG | CTT | CCT | GGT | CAG | AAA | GGA | 574 |
| Gly | Tyr | Pro | Gly | Leu | Leu | Gly | Pro | Pro | Gly | Leu | Pro | Gly | Gln | Lys | Gly | |
| | | 175 | | | | | 180 | | | | | 185 | | | | |
| TCA | AAA | GGT | GAC | CCT | GTC | CTT | GCT | CCA | GGT | AGT | TTC | AAA | GGA | ATT | AAG | 622 |
| Ser | Lys | Gly | Asp | Pro | Val | Leu | Ala | Pro | Gly | Ser | Phe | Lys | Gly | Ile | Lys | |
| 190 | | | | | 195 | | | | | 200 | | | | | 205 | |
| GGG | GAT | CCT | GGG | CTG | CCT | GGA | CTG | GAT | GGA | ATC | ACT | GGC | CCA | CAA | GGA | 670 |
| Gly | Asp | Pro | Gly | Leu | Pro | Gly | Leu | Asp | Gly | Ile | Thr | Gly | Pro | Gln | Gly | |
| | | | | 210 | | | | | 215 | | | | | 220 | | |
| GCA | CCC | GGA | TTT | CCT | GGA | GCT | GTA | GGA | CCT | GCA | GGA | CCA | CCA | GGA | TTA | 718 |
| Ala | Pro | Gly | Phe | Pro | Gly | Ala | Val | Gly | Pro | Ala | Gly | Pro | Pro | Gly | Leu | |
| | | | 225 | | | | | 230 | | | | | 235 | | | |
| CAA | GGT | CCT | CCA | GGG | CCT | CCT | GGT | CCT | CTT | GGT | CCT | GAT | GGG | AAT | ATG | 766 |
| Gln | Gly | Pro | Pro | Gly | Pro | Pro | Gly | Pro | Leu | Gly | Pro | Asp | Gly | Asn | Met | |
| | | 240 | | | | | 245 | | | | | 250 | | | | |
| GGG | CTA | GGT | TTT | CAA | GGA | GAG | AAA | GGA | GTC | AAG | GGG | GAT | GTT | GGC | CTC | 814 |
| Gly | Leu | Gly | Phe | Gln | Gly | Glu | Lys | Gly | Val | Lys | Gly | Asp | Val | Gly | Leu | |
| | 255 | | | | | 260 | | | | | 265 | | | | | |
| CCT | GGC | CCA | GCA | GGA | CCT | CCA | CCA | TCT | ACT | GGA | GAG | CTG | GAA | TTC | ATG | 862 |
| Pro | Gly | Pro | Ala | Gly | Pro | Pro | Pro | Ser | Thr | Gly | Glu | Leu | Glu | Phe | Met | |
| 270 | | | | | 275 | | | | | 280 | | | | | 285 | |
| GGA | TTC | CCC | AAA | GGG | AAG | AAA | GGA | TCC | AAG | GGT | GAA | CCA | GGG | CCT | AAG | 910 |
| Gly | Phe | Pro | Lys | Gly | Lys | Lys | Gly | Ser | Lys | Gly | Glu | Pro | Gly | Pro | Lys | |
| | | | | 290 | | | | | 295 | | | | | 300 | | |
| GGT | TTT | CCA | GGC | ATA | AGT | GGC | CCT | CCA | GGC | TTC | CCG | GGC | CTT | GGA | ACT | 958 |
| Gly | Phe | Pro | Gly | Ile | Ser | Gly | Pro | Pro | Gly | Phe | Pro | Gly | Leu | Gly | Thr | |
| | | | 305 | | | | | 310 | | | | | 315 | | | |
| ACT | GGA | GAA | AAG | GGA | GAA | AAG | GGA | GAA | AAG | GGA | ATC | CCT | GGT | TTG | CCA | 1006 |
| Thr | Gly | Glu | Lys | Gly | Glu | Lys | Gly | Glu | Lys | Gly | Ile | Pro | Gly | Leu | Pro | |
| | | 320 | | | | | 325 | | | | | 330 | | | | |

```
GGA  CCT  AGG  GGT  CCC  ATG  GGT  TCA  GAA  GGA  GTC  CAA  GGC  CCT  CCA  GGG       1054
Gly  Pro  Arg  Gly  Pro  Met  Gly  Ser  Glu  Gly  Val  Gln  Gly  Pro  Pro  Gly
     335            340                      345

CAA  CAG  GGC  AAG  AAA  GGG  ACC  CTG  GGA  TTT  CCT  GGG  CTT  AAT  GGA  TTC       1102
Gln  Gln  Gly  Lys  Lys  Gly  Thr  Leu  Gly  Phe  Pro  Gly  Leu  Asn  Gly  Phe
350                      355                      360                      365

CAA  GGA  ATT  GAG  GGT  CAA  AAG  GGT  GAC  ATT  GGC  CTG  CCA  GGC  CCA  GAT       1150
Gln  Gly  Ile  Glu  Gly  Gln  Lys  Gly  Asp  Ile  Gly  Leu  Pro  Gly  Pro  Asp
                    370                      375                      380

GTT  TTC  ATC  GAT  ATA  GAT  GGT  GCT  GTG  ATC  TCA  GGT  AAT  CCT  GGA  GAT       1198
Val  Phe  Ile  Asp  Ile  Asp  Gly  Ala  Val  Ile  Ser  Gly  Asn  Pro  Gly  Asp
               385                      390                      395

CCT  GGT  GTA  CCT  GGC  CTC  CCA  GGC  CTT  AAA  GGA  GAT  GAA  GGC  ATC  CAA       1246
Pro  Gly  Val  Pro  Gly  Leu  Pro  Gly  Leu  Lys  Gly  Asp  Glu  Gly  Ile  Gln
          400                      405                      410

GGC  CTA  CGT  GGC  CCT  TCT  GGT  GTC  CCT  GGA  TTG  CCA  GCA  TTA  TCA  GGT       1294
Gly  Leu  Arg  Gly  Pro  Ser  Gly  Val  Pro  Gly  Leu  Pro  Ala  Leu  Ser  Gly
     415                      420                      425

GTC  CCA  GGA  GCC  CTA  GGG  CCT  CAG  GGA  TTT  CCA  GGG  CTG  AAG  GGG  GAC       1342
Val  Pro  Gly  Ala  Leu  Gly  Pro  Gln  Gly  Phe  Pro  Gly  Leu  Lys  Gly  Asp
430                      435                      440                      445

CAA  GGA  AAC  CCA  GGC  CGT  ACC  ACA  ATT  GGA  GCA  GCT  GGC  CTC  CCT  GGC       1390
Gln  Gly  Asn  Pro  Gly  Arg  Thr  Thr  Ile  Gly  Ala  Ala  Gly  Leu  Pro  Gly
                    450                      455                      460

AGA  GAT  GGT  TTG  CCA  GGC  CCA  CCA  GGT  CCA  CCA  GGC  CCA  CCT  AGT  CCA       1438
Arg  Asp  Gly  Leu  Pro  Gly  Pro  Pro  Gly  Pro  Pro  Gly  Pro  Pro  Ser  Pro
               465                      470                      475

GAA  TTT  GAG  ACT  GAA  ACT  CTA  CAC  AAC  AAA  GAG  TCA  GGG  TTC  CCT  GGT       1486
Glu  Phe  Glu  Thr  Glu  Thr  Leu  His  Asn  Lys  Glu  Ser  Gly  Phe  Pro  Gly
          480                      485                      490

CTC  CGA  GGA  GAA  CAA  GGT  CCA  AAA  GGA  AAC  CTA  GGC  CTC  AAA  GGA  ATA       1534
Leu  Arg  Gly  Glu  Gln  Gly  Pro  Lys  Gly  Asn  Leu  Gly  Leu  Lys  Gly  Ile
     495                      500                      505

AAA  GGA  GAC  TCA  GGT  TTC  TGT  GCT  TGT  GAC  GGT  GGT  GTT  CCC  AAC  ACT       1582
Lys  Gly  Asp  Ser  Gly  Phe  Cys  Ala  Cys  Asp  Gly  Gly  Val  Pro  Asn  Thr
510                      515                      520                      525

GGA  CCA  CCC  GGG  GAA  CCA  GGC  CCA  CCT  GGT  CCA  TGG  GGT  CTC  ATA  GGC       1630
Gly  Pro  Pro  Gly  Glu  Pro  Gly  Pro  Pro  Gly  Pro  Trp  Gly  Leu  Ile  Gly
                    530                      535                      540

CTT  CCA  GGC  CTT  AAA  GGA  GCC  AGA  GGA  GAT  CGA  GGC  TCT  GGG  GGT  GCA       1678
Leu  Pro  Gly  Leu  Lys  Gly  Ala  Arg  Gly  Asp  Arg  Gly  Ser  Gly  Gly  Ala
               545                      550                      555

CAG  GGC  CCA  GCA  GGG  GCT  CCA  GGC  TTA  GTT  GGG  CCT  CTG  GGT  CCT  TCA       1726
Gln  Gly  Pro  Ala  Gly  Ala  Pro  Gly  Leu  Val  Gly  Pro  Leu  Gly  Pro  Ser
          560                      565                      570

GGA  CCC  AAA  GGA  AAG  AAG  GGG  GAA  CCA  ATT  CTC  AGT  ACA  ATC  CAA  GGA       1774
Gly  Pro  Lys  Gly  Lys  Lys  Gly  Glu  Pro  Ile  Leu  Ser  Thr  Ile  Gln  Gly
     575                      580                      585

ATG  CCA  GGA  GAT  CGG  GGT  GAT  TCT  GGC  TCC  CAG  GGC  TTC  CGT  GGT  GTA       1822
Met  Pro  Gly  Asp  Arg  Gly  Asp  Ser  Gly  Ser  Gln  Gly  Phe  Arg  Gly  Val
590                      595                      600                      605

ATA  GGA  GAA  CCA  GGC  AAG  GAC  GGA  GTA  CCA  GGT  TTA  CCA  GGT  CTG  CCA       1870
Ile  Gly  Glu  Pro  Gly  Lys  Asp  Gly  Val  Pro  Gly  Leu  Pro  Gly  Leu  Pro
                    610                      615                      620

GGC  CTT  CCG  GGT  GAT  GGT  GGA  CAG  GGC  TTC  CCA  GGT  GAA  AAG  GGG  TTA       1918
Gly  Leu  Pro  Gly  Asp  Gly  Gly  Gln  Gly  Phe  Pro  Gly  Glu  Lys  Gly  Leu
               625                      630                      635

CCT  GGA  CTT  CCT  GGT  GAA  AAA  GGC  CAT  CCT  GGT  CCA  CCT  GGC  CTC  CCA       1966
Pro  Gly  Leu  Pro  Gly  Glu  Lys  Gly  His  Pro  Gly  Pro  Pro  Gly  Leu  Pro
          640                      645                      650
```

-continued

| | | | | | | | | | | | | | | | | |
|---|---|---|---|---|---|---|---|---|---|---|---|---|---|---|---|---|
| GGA | AAT | GGG | TTA | CCA | GGA | CTT | CCT | GGA | CCC | CGT | GGG | CTT | CCT | GGA | GAT | 2014 |
| Gly | Asn 655 | Gly | Leu | Pro | Gly 660 | Leu | Pro | Gly | Pro | Arg 665 | Gly | Leu | Pro | Gly | Asp | |
| AAA | GGC | AAG | GAT | GGA | TTA | CCG | GGA | CAA | CAA | GGC | CTT | CCC | GGA | TCT | AAG | 2062 |
| Lys 670 | Gly | Lys | Asp | Gly | Leu 675 | Pro | Gly | Gln | Gln | Gly 680 | Leu | Pro | Gly | Ser | Lys 685 | |
| GGA | ATC | ACC | CTG | CCC | TGT | ATT | ATT | CCT | GGG | TCA | TAC | GGT | CCA | TCA | GGA | 2110 |
| Gly | Ile | Thr | Leu | Pro 690 | Cys | Ile | Ile | Pro | Gly 695 | Ser | Tyr | Gly | Pro | Ser 700 | Gly | |
| TTT | CCA | GGC | ACT | CCC | GGA | TTC | CCA | GGC | CCT | AAA | GGG | TCT | CGA | GGC | CTC | 2158 |
| Phe | Pro | Gly | Thr 705 | Pro | Gly | Phe | Pro | Gly 710 | Pro | Lys | Gly | Ser | Arg 715 | Gly | Leu | |
| CCT | GGG | ACC | CCA | GGC | CAG | CCT | GGG | TCA | AGT | GGA | AGT | AAA | GGA | GAG | CCA | 2206 |
| Pro | Gly | Thr 720 | Pro | Gly | Gln | Pro | Gly 725 | Ser | Ser | Gly | Ser | Lys 730 | Gly | Glu | Pro | |
| GGG | AGT | CCA | GGA | TTG | GTT | CAT | CTT | CCT | GAA | TTA | CCA | GGA | TTT | CCT | GGA | 2254 |
| Gly | Ser 735 | Pro | Gly | Leu | Val 740 | His | Leu | Pro | Glu | Leu 745 | Pro | Gly | Phe | Pro | Gly | |
| CCT | CGT | GGG | GAG | AAG | GGC | TTG | CCT | GGG | TTT | CCT | GGG | CTC | CCT | GGA | AAA | 2302 |
| Pro 750 | Arg | Gly | Glu | Lys | Gly 755 | Leu | Pro | Gly | Phe | Pro 760 | Gly | Leu | Pro | Gly | Lys 765 | |
| GAT | GGC | TTG | CCT | GGG | ATG | ATT | GGC | AGT | CCA | GGC | TTA | CCT | GGT | TCC | AAG | 2350 |
| Asp | Gly | Leu | Pro | Gly 770 | Met | Ile | Gly | Ser | Pro 775 | Gly | Leu | Pro | Gly | Ser 780 | Lys | |
| GGA | GCC | ACT | GGT | GAC | ATC | TTT | GGT | GCT | GAA | AAT | GGT | GCT | CCG | GGG | GAA | 2398 |
| Gly | Ala | Thr | Gly 785 | Asp | Ile | Phe | Gly | Ala 790 | Glu | Asn | Gly | Ala | Pro 795 | Gly | Glu | |
| CAA | GGC | CTA | CAA | GGA | TTA | ACA | GGG | CAC | AAA | GGA | TTT | CTT | GGA | GAC | TCT | 2446 |
| Gln | Gly | Leu 800 | Gln | Gly | Leu | Thr | Gly 805 | His | Lys | Gly | Phe | Leu 810 | Gly | Asp | Ser | |
| GGC | CTT | CCA | GGA | CTC | AAG | GGT | GTG | CAC | GGG | AAG | CCT | GGC | TTA | CTA | GGC | 2494 |
| Gly | Leu 815 | Pro | Gly | Leu | Lys 820 | Gly | Val | His | Gly | Lys 825 | Pro | Gly | Leu | Leu | Gly | |
| CCC | AAA | GGT | GAG | CGG | GGC | AGC | CCT | GGG | ACA | CCA | GGA | CAG | GTG | GGA | CAG | 2542 |
| Pro | Lys 830 | Gly | Glu | Arg | Gly 835 | Ser | Pro | Gly | Thr | Pro 840 | Gly | Gln | Val | Gly | Gln 845 | |
| CCA | GGC | ACC | CCA | GGA | TCT | AGT | GGT | CCA | TAT | GGC | ATC | AAG | GGC | AAA | TCT | 2590 |
| Pro | Gly | Thr | Pro | Gly 850 | Ser | Ser | Gly | Pro | Tyr 855 | Gly | Ile | Lys | Gly | Lys 860 | Ser | |
| GGG | CTC | CCA | GGA | GCA | CCA | GGC | TTC | CCA | GGC | ATC | TCA | GGA | CAT | CCT | GGA | 2638 |
| Gly | Leu | Pro | Gly 865 | Ala | Pro | Gly | Phe | Pro 870 | Gly | Ile | Ser | Gly | His 875 | Pro | Gly | |
| AAG | AAA | GGA | ACA | AGA | GGC | AAG | AAA | GGT | CCT | CCT | GGA | TCA | ATT | GTA | AAG | 2686 |
| Lys | Lys | Gly 880 | Thr | Arg | Gly | Lys | Lys 885 | Gly | Pro | Pro | Gly | Ser 890 | Ile | Val | Lys | |
| AAA | GGG | CTG | CCA | GGG | CTA | AAA | GGC | CTT | CCT | GGA | AAT | CCA | GGC | CTA | GTA | 2734 |
| Lys | Gly 895 | Leu | Pro | Gly | Leu 900 | Lys | Gly | Leu | Pro | Gly 905 | Asn | Pro | Gly | Leu | Val | |
| GGA | CTG | AAA | GGA | AGC | CCA | GGC | TCT | CCA | GGG | GTC | GCT | GGG | TTG | CCA | GCC | 2782 |
| Gly | Leu 910 | Lys | Gly | Ser | Pro 915 | Gly | Ser | Pro | Gly | Val 920 | Ala | Gly | Leu | Pro | Ala 925 | |
| CTC | TCT | GGA | CCC | AAG | GGA | GAG | AAG | GGG | TCT | GTT | GGA | TTC | GTA | GGT | TTT | 2830 |
| Leu | Ser | Gly | Pro | Lys 930 | Gly | Glu | Lys | Gly | Ser 935 | Val | Gly | Phe | Val | Gly 940 | Phe | |
| CCA | GGA | ATA | CCA | GGT | CTG | CCT | GGT | ATT | CCT | GGA | ACA | AGA | GGA | TTA | AAA | 2878 |
| Pro | Gly | Ile | Pro 945 | Gly | Leu | Pro | Gly | Ile 950 | Pro | Gly | Thr | Arg | Gly 955 | Leu | Lys | |
| GGA | ATT | CCA | GGA | TCA | ACT | GGA | AAA | ATG | GGA | CCA | TCT | GGA | CGC | GCT | GGT | 2926 |
| Gly | Ile | Pro | Gly 960 | Ser | Thr | Gly | Lys | Met 965 | Gly | Pro | Ser | Gly | Arg 970 | Ala | Gly | |

-continued

| | | | | | | | | | | | | | | | | |
|---|---|---|---|---|---|---|---|---|---|---|---|---|---|---|---|---|
| ACT | CCT | GGT | GAA | AAG | GGA | GAC | AGA | GGC | AAT | CCG | GGG | CCA | GTC | GGA | ATA | 2974 |
| Thr | Pro | Gly | Glu | Lys | Gly | Asp | Arg | Gly | Asn | Pro | Gly | Pro | Val | Gly | Ile | |
| | 975 | | | | | 980 | | | | | 985 | | | | | |
| CCT | AGT | CCA | AGA | CGT | CCA | ATG | TCA | AAC | CTT | TGG | CTC | AAA | GGA | GAC | AAA | 3022 |
| Pro | Ser | Pro | Arg | Arg | Pro | Met | Ser | Asn | Leu | Trp | Leu | Lys | Gly | Asp | Lys | |
| 990 | | | | | 995 | | | | | 1000 | | | | | 1005 | |
| GGC | TCT | CAA | GGC | TCA | GCC | GGA | TCC | AAT | GGA | TTT | CCT | GGG | CCA | AGA | GGT | 3070 |
| Gly | Ser | Gln | Gly | Ser | Ala | Gly | Ser | Asn | Gly | Phe | Pro | Gly | Pro | Arg | Gly | |
| | | | | 1010 | | | | | 1015 | | | | | 1020 | | |
| GAC | AAA | GGA | GAG | GCT | GGT | CGA | CCT | GGA | CCA | CCA | GGC | CTA | CCT | GGA | GCT | 3118 |
| Asp | Lys | Gly | Glu | Ala | Gly | Arg | Pro | Gly | Pro | Pro | Gly | Leu | Pro | Gly | Ala | |
| | | | 1025 | | | | | 1030 | | | | | 1035 | | | |
| CCT | GGC | CTC | CCA | GGC | ATT | ATC | AAA | GGA | GTT | AGT | GGA | AAG | CCA | GGG | CCC | 3166 |
| Pro | Gly | Leu | Pro | Gly | Ile | Ile | Lys | Gly | Val | Ser | Gly | Lys | Pro | Gly | Pro | |
| | | 1040 | | | | | 1045 | | | | | 1050 | | | | |
| CCT | GGC | TTC | ATG | GGA | ATC | CGG | GGT | TTA | CCT | GGC | CTG | AAG | GGG | TCC | TCT | 3214 |
| Pro | Gly | Phe | Met | Gly | Ile | Arg | Gly | Leu | Pro | Gly | Leu | Lys | Gly | Ser | Ser | |
| | | 1055 | | | | | 1060 | | | | | 1065 | | | | |
| GGG | ATC | ACA | GGT | TTC | CCA | GGA | ATG | CCA | GGA | GAA | AGT | GGT | TCA | CAA | GGT | 3262 |
| Gly | Ile | Thr | Gly | Phe | Pro | Gly | Met | Pro | Gly | Glu | Ser | Gly | Ser | Gln | Gly | |
| 1070 | | | | | 1075 | | | | | 1080 | | | | | 1085 | |
| ATC | AGA | GGG | TCG | CCT | GGA | CTC | CCA | GGA | GCA | TCT | GGT | CTC | CCA | GGC | CTG | 3310 |
| Ile | Arg | Gly | Ser | Pro | Gly | Leu | Pro | Gly | Ala | Ser | Gly | Leu | Pro | Gly | Leu | |
| | | | | 1090 | | | | | 1095 | | | | | 1100 | | |
| AAA | GGA | GAC | AAC | GGC | CAG | ACA | GTT | GAA | ATT | TCC | GGT | AGC | CCA | GGA | CCC | 3358 |
| Lys | Gly | Asp | Asn | Gly | Gln | Thr | Val | Glu | Ile | Ser | Gly | Ser | Pro | Gly | Pro | |
| | | | | 1105 | | | | | 1110 | | | | | 1115 | | |
| AAG | GGA | CAG | CCT | GGC | GAA | TCT | GGT | TTT | AAA | GGC | ACA | AAA | GGA | AGA | GAT | 3406 |
| Lys | Gly | Gln | Pro | Gly | Glu | Ser | Gly | Phe | Lys | Gly | Thr | Lys | Gly | Arg | Asp | |
| | | | 1120 | | | | | 1125 | | | | | 1130 | | | |
| GGA | CTA | ATA | GGC | AAT | ATA | GGC | TTC | CCT | GGA | AAC | AAA | GGT | GAA | GAT | GGA | 3454 |
| Gly | Leu | Ile | Gly | Asn | Ile | Gly | Phe | Pro | Gly | Asn | Lys | Gly | Glu | Asp | Gly | |
| | 1135 | | | | | 1140 | | | | | 1145 | | | | | |
| AAA | GTT | GGT | GTT | TCT | GGA | GAT | GTT | GGC | CTT | CCT | GGA | GCT | CCA | GGA | TTT | 3502 |
| Lys | Val | Gly | Val | Ser | Gly | Asp | Val | Gly | Leu | Pro | Gly | Ala | Pro | Gly | Phe | |
| 1150 | | | | | 1155 | | | | | 1160 | | | | | 1165 | |
| CCA | GGA | GTT | GCC | GGC | ATG | AGA | GGA | GAA | CCA | GGA | CTT | CCA | GGT | TCT | TCT | 3550 |
| Pro | Gly | Val | Ala | Gly | Met | Arg | Gly | Glu | Pro | Gly | Leu | Pro | Gly | Ser | Ser | |
| | | | | 1170 | | | | | 1175 | | | | | 1180 | | |
| GGT | CAC | CAA | GGG | GCA | ATT | GGG | CCT | CTA | GGA | TCC | CCC | GGA | TTA | ATA | GGA | 3598 |
| Gly | His | Gln | Gly | Ala | Ile | Gly | Pro | Leu | Gly | Ser | Pro | Gly | Leu | Ile | Gly | |
| | | | | 1185 | | | | | 1190 | | | | | 1195 | | |
| CCC | AAA | GGC | TTC | CCT | GGA | TTT | CCT | GGT | TTA | CAT | GGA | CTG | AAT | GGG | CTT | 3646 |
| Pro | Lys | Gly | Phe | Pro | Gly | Phe | Pro | Gly | Leu | His | Gly | Leu | Asn | Gly | Leu | |
| | | 1200 | | | | | 1205 | | | | | 1210 | | | | |
| CCG | GGC | ACC | AAG | GGT | ACC | CAT | GGC | ACT | CCA | GGA | CCT | AGT | ATC | ACC | GGT | 3694 |
| Pro | Gly | Thr | Lys | Gly | Thr | His | Gly | Thr | Pro | Gly | Pro | Ser | Ile | Thr | Gly | |
| | 1215 | | | | | 1220 | | | | | 1225 | | | | | |
| GTG | CCT | GGG | CCT | GCT | GGT | CTC | CCT | GGA | CCC | AAA | GGA | GAA | AAA | GGA | TAT | 3742 |
| Val | Pro | Gly | Pro | Ala | Gly | Leu | Pro | Gly | Pro | Lys | Gly | Glu | Lys | Gly | Tyr | |
| 1230 | | | | | 1235 | | | | | 1240 | | | | | 1245 | |
| CCA | GGA | ATT | GGC | ATC | GGA | GCT | CCA | GGG | AAG | CCG | GGC | CTG | AGA | GGG | CAA | 3790 |
| Pro | Gly | Ile | Gly | Ile | Gly | Ala | Pro | Gly | Lys | Pro | Gly | Leu | Arg | Gly | Gln | |
| | | | | 1250 | | | | | 1255 | | | | | 1260 | | |
| AAA | GGT | GAT | CGA | GGT | TTC | CCA | GGT | CTC | CAG | GGC | CCT | GCT | GGT | CTC | CCC | 3838 |
| Lys | Gly | Asp | Arg | Gly | Phe | Pro | Gly | Leu | Gln | Gly | Pro | Ala | Gly | Leu | Pro | |
| | | | 1265 | | | | | 1270 | | | | | 1275 | | | |
| GGT | GCC | CCA | GGC | ATC | TCC | TTG | CCC | TCA | CTC | ATA | GCA | GGA | CAG | CCT | GGT | 3886 |
| Gly | Ala | Pro | Gly | Ile | Ser | Leu | Pro | Ser | Leu | Ile | Ala | Gly | Gln | Pro | Gly | |
| | | 1280 | | | | | 1285 | | | | | 1290 | | | | |

```
GAC CCC GGG CGA CCA GGC CTA GAT GGA GAA CGA GGC CGC CCA GGC CCC         3934
Asp Pro Gly Arg Pro Gly Leu Asp Gly Glu Arg Gly Arg Pro Gly Pro
1295                1300                1305

GCT GGA CCC CCA GGT CCC CCT GGG CCA TCC TCG AAT CAA GGC GAC ACC         3982
Ala Gly Pro Pro Gly Pro Pro Gly Pro Ser Ser Asn Gln Gly Asp Thr
1310                1315                1320                1325

GGA GAC CCT GGC TTC CCT GGA ATT CCT GGA CCT AAA GGG CCT AAG GGA         4030
Gly Asp Pro Gly Phe Pro Gly Ile Pro Gly Pro Lys Gly Pro Lys Gly
                1330                1335                1340

GAC CAA GGA ATT CCA GGT TTT TCT GGC CTC CCT GGA GAG CTA GGA CTG         4078
Asp Gln Gly Ile Pro Gly Phe Ser Gly Leu Pro Gly Glu Leu Gly Leu
1345                1350                1355

AAA GGC TCT TCT GGC CTC CAA GGT GAT CCT GGA CAA ACA CCA ACT GCA         4126
Lys Gly Ser Ser Gly Leu Gln Gly Asp Pro Gly Gln Thr Pro Thr Ala
                1360                1365                1370

GAA GCT GTC CAG GTT CCT CCT GGA CCC TTG GGT CTA CCA GGG ATC GAT         4174
Glu Ala Val Gln Val Pro Pro Gly Pro Leu Gly Leu Pro Gly Ile Asp
1375                1380                1385

GGC ATC CCT GGC CTC ACT GGG GAC CCT GGG GCT CAA GGC CCT GTA GGC         4222
Gly Ile Pro Gly Leu Thr Gly Asp Pro Gly Ala Gln Gly Pro Val Gly
1390                1395                1400                1405

CTA CAA GGC TCC AAA GGT TTA CCT GGC ATC CCC GGT AAA GAT GGT CCC         4270
Leu Gln Gly Ser Lys Gly Leu Pro Gly Ile Pro Gly Lys Asp Gly Pro
                1410                1415                1420

AGT GGG CTC CCA GGC CCA CCT GGG GCT CTT GGT GAT CCT GGT CTG CCT         4318
Ser Gly Leu Pro Gly Pro Pro Gly Ala Leu Gly Asp Pro Gly Leu Pro
                1425                1430                1435

GGA CTG CAA GGC CCT CCA GGA TTT GAA GGA GCT CCA GGG CAG CAA GGC         4366
Gly Leu Gln Gly Pro Pro Gly Phe Glu Gly Ala Pro Gly Gln Gln Gly
1440                1445                1450

CCT TCG GGA TGC CTG GAA TGC CTG GCC AGA GCA TGA GAG TGG GCT ACA         4414
Pro Ser Gly Cys Leu Glu Cys Leu Ala Arg Ala     Glu Trp Ala Thr
1455                1460                    1465

CGT TGG TAA AGC ACA GCC AGT CGG AAC AGG TGC CCC CGT GTC CCA TCG         4462
Arg Trp     Ser Thr Ala Ser Arg Asn Arg Cys Pro Arg Val Pro Ser
1470                1475                1480

GGA TGA GCC AGC TGT GGG TGG GGT ACA GCT ACT GTT TGT GGA GGG GC         4510
Gly     Ala Ser Cys Gly Trp Gly Thr Ala Tyr Cys Leu Trp Arg Gly
        1485                1490                1495

AAC ACA AAG CCC ACA ACC AGG ACC TGG GCT TTG CTG GCT CCT GTC TGC         4558
Asn Thr Lys Pro Thr Thr Arg Thr Trp Ala Leu Leu Ala Pro Val Cys
1500                1505                1510

CCC GCT TCA GCA CCA TGC CCT CAC TAC TGC AAC ATC AAC GAG GTG TGC         4606
Pro Ala Ser Ala Pro Cys Pro His Tyr Cys Asn Ile Asn Glu Val Cys
1515                1520                1525                1530

CAC TAT GCC AGG CGC AAT GAT AAA TCT TAC TGG CTC TCC ACT ACC GCC         4654
His Tyr Ala Arg Arg Asn Asp Lys Ser Tyr Trp Leu Ser Thr Thr Ala
                1535                1540                1545

CCT ATC CCC ATG ATG CCC GTC AGC CAG ACC CAG ATT CCC CAG TAC ATC         4702
Pro Ile Pro Met Met Pro Val Ser Gln Thr Gln Ile Pro Gln Tyr Ile
                1550                1555                1560

AGC CGC TGC TCT GTG TGT GAG GCA CCC TCG AAG CCA TTC TGT GCA CAG         4750
Ser Arg Cys Ser Val Cys Glu Ala Pro Ser Lys Pro Phe Cys Ala Gln
        1565                1570                1575

CCA GGA CAT CAC CAT CCC GCA GTG CCC CCT GGG CTG GCG CAG CCT CTG         4798
Pro Gly His His His Pro Ala Val Pro Pro Gly Leu Ala Gln Pro Leu
        1580                1585                1590

GAT TGG GTA CTC TTT CCT CAT GCA CAC TGC CGC TGG TGC CGA GGG TGG         4846
Asp Trp Val Leu Phe Pro His Ala His Cys Arg Trp Cys Arg Gly Trp
1595                1600                1605                1610
```

```
AGG CAG TCC CTG GTC TCA CCT GGC TCC TCC TAG AGG ACT TTC GGG CCA      4894
Arg Gln Ser Leu Val Ser Pro Gly Ser Ser     Arg Thr Phe Gly Pro
            1615            1620                            1625

CTC CTT TCA TCG AAT GCA GTG GCC CGA GGC ACC TGC CAC TAC TTT GCA      4942
Leu Leu Ser Ser Asn Ala Val Ala Arg Gly Thr Cys His Tyr Phe Ala
                1630            1635                    1640

AAC AAG TAC AGT TTC TGG TTG ACC ACA GTG GAG GAG AGG CAG CAG TTT      4990
Asn Lys Tyr Ser Phe Trp Leu Thr Thr Val Glu Glu Arg Gln Gln Phe
            1645            1650                    1655

GGG GAG TTG CCT GTG TCT GAA ACG CTG AAA GCT GGG CAG CTC CAC ACT      5038
Gly Glu Leu Pro Val Ser Glu Thr Leu Lys Ala Gly Gln Leu His Thr
        1660            1665                    1670

CGA GTC AGT CGC TGC CAG GTG TGT ATG AAC CGG AAT TCC AGC TGG CGC      5086
Arg Val Ser Arg Cys Gln Val Cys Met Asn Arg Asn Ser Ser Trp Arg
        1675            1680                    1685

CGG TCG CTC CAT TCC A                                                5102
Arg Ser Leu His Ser
1690
```

(2) INFORMATION FOR SEQ ID NO:2:

(i) SEQUENCE CHARACTERISTICS:
        (A) LENGTH: 1694 amino acids
        (B) TYPE: amino acid
        (D) TOPOLOGY: linear (ii) MOLECULE TYPE: protein (xi) SEQUENCE DESCRIPTION: SEQ ID NO:2:

```
Ile Pro Val Pro Gly Leu Leu Val Phe Phe Thr Phe Gln Leu Leu Thr
 1               5                   10                  15

Glu Gln Arg Val Ser Thr Tyr Lys Gln Lys Met Lys Tyr Trp Glu Ile
            20                  25                  30

Lys Tyr Met Leu Ile Asn Lys Leu Trp Leu Leu Leu Val Thr Leu Cys
            35                  40                  45

Leu Thr Glu Glu Leu Ala Ala Ala Gly Glu Lys Ser Tyr Gly Lys Pro
        50                  55                  60

Cys Gly Gly Gln Asp Cys Ser Gly Ser Cys Gln Cys Phe Pro Glu Lys
 65                  70                  75                  80

Gly Ala Arg Gly Arg Pro Gly Pro Ile Gly Ile Gln Gly Pro Thr Gly
                85                  90                  95

Pro Gln Gly Phe Thr Gly Ser Thr Gly Leu Ser Gly Leu Lys Gly Glu
            100                 105                 110

Arg Gly Phe Pro Gly Leu Leu Gly Pro Tyr Gly Pro Lys Gly Asp Lys
        115                 120                 125

Gly Pro Met Gly Val Pro Gly Phe Leu Gly Ile Asn Gly Ile Pro Gly
    130                 135                 140

His Pro Gly Gln Pro Gly Pro Arg Gly Pro Pro Gly Leu Asp Gly Cys
145                 150                 155                 160

Asn Gly Thr Gln Gly Ala Val Gly Phe Pro Gly Pro Asp Gly Tyr Pro
                165                 170                 175

Gly Leu Leu Gly Pro Pro Gly Leu Pro Gly Gln Lys Gly Ser Lys Gly
            180                 185                 190

Asp Pro Val Leu Ala Pro Gly Ser Phe Lys Gly Ile Lys Gly Asp Pro
        195                 200                 205

Gly Leu Pro Gly Leu Asp Gly Ile Thr Gly Pro Gln Gly Ala Pro Gly
    210                 215                 220

Phe Pro Gly Ala Val Gly Pro Ala Gly Pro Pro Gly Leu Gln Gly Pro
```

-continued

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |
| Pro | Gly | Pro | Pro | Gly | Pro | Leu | Gly | Pro | Asp | Gly | Asn | Met | Gly | Leu | Gly |
|     |     |     |     |     | 245 |     |     |     |     | 250 |     |     |     |     | 255 |
| Phe | Gln | Gly | Glu | Lys | Gly | Val | Lys | Gly | Asp | Val | Gly | Leu | Pro | Gly | Pro |
|     |     |     |     |     | 260 |     |     |     |     | 265 |     |     |     |     | 270 |
| Ala | Gly | Pro | Pro | Ser | Thr | Gly | Glu | Leu | Glu | Phe | Met | Gly | Phe | Pro |
|     |     |     | 275 |     |     |     | 280 |     |     |     | 285 |
| Lys | Gly | Lys | Lys | Gly | Ser | Lys | Gly | Glu | Pro | Gly | Pro | Lys | Gly | Phe | Pro |
|     |     | 290 |     |     |     |     | 295 |     |     |     |     | 300 |
| Gly | Ile | Ser | Gly | Pro | Pro | Gly | Phe | Pro | Gly | Leu | Gly | Thr | Thr | Gly | Glu |
| 305 |     |     |     |     | 310 |     |     |     |     | 315 |     |     |     |     | 320 |
| Lys | Gly | Glu | Lys | Gly | Glu | Lys | Gly | Ile | Pro | Gly | Leu | Pro | Gly | Pro | Arg |
|     |     |     |     | 325 |     |     |     |     | 330 |     |     |     |     | 335 |
| Gly | Pro | Met | Gly | Ser | Glu | Gly | Val | Gln | Gly | Pro | Pro | Gly | Gln | Gln | Gly |
|     |     |     | 340 |     |     |     | 345 |     |     |     |     | 350 |
| Lys | Lys | Gly | Thr | Leu | Gly | Phe | Pro | Gly | Leu | Asn | Gly | Phe | Gln | Gly | Ile |
|     |     | 355 |     |     |     |     | 360 |     |     |     | 365 |
| Glu | Gly | Gln | Lys | Gly | Asp | Ile | Gly | Leu | Pro | Gly | Pro | Asp | Val | Phe | Ile |
|     | 370 |     |     |     |     | 375 |     |     |     |     | 380 |
| Asp | Ile | Asp | Gly | Ala | Val | Ile | Ser | Gly | Asn | Pro | Gly | Asp | Pro | Gly | Val |
| 385 |     |     |     |     | 390 |     |     |     |     | 395 |     |     |     |     | 400 |
| Pro | Gly | Leu | Pro | Gly | Leu | Lys | Gly | Asp | Glu | Gly | Ile | Gln | Gly | Leu | Arg |
|     |     |     |     | 405 |     |     |     |     | 410 |     |     |     |     | 415 |
| Gly | Pro | Ser | Gly | Val | Pro | Gly | Leu | Pro | Ala | Leu | Ser | Gly | Val | Pro | Gly |
|     |     |     | 420 |     |     |     |     | 425 |     |     |     |     | 430 |
| Ala | Leu | Gly | Pro | Gln | Gly | Phe | Pro | Gly | Leu | Lys | Gly | Asp | Gln | Gly | Asn |
|     |     | 435 |     |     |     |     | 440 |     |     |     |     | 445 |
| Pro | Gly | Arg | Thr | Thr | Ile | Gly | Ala | Ala | Gly | Leu | Pro | Gly | Arg | Asp | Gly |
|     |     | 450 |     |     |     |     | 455 |     |     |     |     | 460 |
| Leu | Pro | Gly | Pro | Pro | Gly | Pro | Pro | Gly | Pro | Pro | Ser | Pro | Glu | Phe | Glu |
| 465 |     |     |     |     | 470 |     |     |     |     | 475 |     |     |     |     | 480 |
| Thr | Glu | Thr | Leu | His | Asn | Lys | Glu | Ser | Gly | Phe | Pro | Gly | Leu | Arg | Gly |
|     |     |     |     | 485 |     |     |     |     | 490 |     |     |     |     | 495 |
| Glu | Gln | Gly | Pro | Lys | Gly | Asn | Leu | Gly | Leu | Lys | Gly | Ile | Lys | Gly | Asp |
|     |     |     | 500 |     |     |     |     | 505 |     |     |     |     | 510 |
| Ser | Gly | Phe | Cys | Ala | Cys | Asp | Gly | Gly | Val | Pro | Asn | Thr | Gly | Pro | Pro |
|     |     | 515 |     |     |     |     | 520 |     |     |     |     | 525 |
| Gly | Glu | Pro | Gly | Pro | Pro | Gly | Pro | Trp | Gly | Leu | Ile | Gly | Leu | Pro | Gly |
|     | 530 |     |     |     |     | 535 |     |     |     |     | 540 |
| Leu | Lys | Gly | Ala | Arg | Gly | Asp | Arg | Gly | Ser | Gly | Gly | Ala | Gln | Gly | Pro |
| 545 |     |     |     |     | 550 |     |     |     |     | 555 |     |     |     |     | 560 |
| Ala | Gly | Ala | Pro | Gly | Leu | Val | Gly | Pro | Leu | Gly | Pro | Ser | Gly | Pro | Lys |
|     |     |     |     | 565 |     |     |     |     | 570 |     |     |     |     | 575 |
| Gly | Lys | Lys | Gly | Glu | Pro | Ile | Leu | Ser | Thr | Ile | Gln | Gly | Met | Pro | Gly |
|     |     |     | 580 |     |     |     |     | 585 |     |     |     |     | 590 |
| Asp | Arg | Gly | Asp | Ser | Gly | Ser | Gln | Gly | Phe | Arg | Gly | Val | Ile | Gly | Glu |
|     |     | 595 |     |     |     |     | 600 |     |     |     |     | 605 |
| Pro | Gly | Lys | Asp | Gly | Val | Pro | Gly | Leu | Pro | Gly | Leu | Pro | Gly | Leu | Pro |
|     |     | 610 |     |     |     |     | 615 |     |     |     |     | 620 |
| Gly | Asp | Gly | Gly | Gln | Gly | Phe | Pro | Gly | Glu | Lys | Gly | Leu | Pro | Gly | Leu |
| 625 |     |     |     |     | 630 |     |     |     |     | 635 |     |     |     |     | 640 |
| Pro | Gly | Glu | Lys | Gly | His | Pro | Gly | Pro | Pro | Gly | Leu | Pro | Gly | Asn | Gly |
|     |     |     |     | 645 |     |     |     |     | 650 |     |     |     |     | 655 |

-continued

| | | | | | | | | | | | | | |
|---|---|---|---|---|---|---|---|---|---|---|---|---|---|
| Leu | Pro | Gly | Leu 660 | Pro | Gly | Pro | Arg 665 | Gly | Leu | Pro | Gly | Asp 670 | Lys | Gly | Lys |
| Asp | Gly | Leu 675 | Pro | Gly | Gln | Gln 680 | Gly | Leu | Pro | Gly | Ser 685 | Lys | Gly | Ile | Thr |
| Leu | Pro 690 | Cys | Ile | Ile | Pro | Gly 695 | Ser | Tyr | Gly | Pro | Ser 700 | Gly | Phe | Pro | Gly |
| Thr 705 | Pro | Gly | Phe | Pro | Gly 710 | Pro | Lys | Gly | Ser | Arg 715 | Gly | Leu | Pro | Gly | Thr 720 |
| Pro | Gly | Gln | Pro | Gly 725 | Ser | Ser | Gly | Ser | Lys 730 | Gly | Glu | Pro | Gly | Ser 735 | Pro |
| Gly | Leu | Val | His 740 | Leu | Pro | Glu | Leu 745 | Pro | Gly | Phe | Pro | Gly 750 | Pro | Arg | Gly |
| Glu | Lys | Gly 755 | Leu | Pro | Gly | Phe 760 | Pro | Gly | Leu | Pro | Gly 765 | Lys | Asp | Gly | Leu |
| Pro | Gly 770 | Met | Ile | Gly | Ser | Pro 775 | Gly | Leu | Pro | Gly | Ser 780 | Lys | Gly | Ala | Thr |
| Gly 785 | Asp | Ile | Phe | Gly | Ala 790 | Glu | Asn | Gly | Ala | Pro 795 | Gly | Glu | Gln | Gly | Leu 800 |
| Gln | Gly | Leu | Thr | Gly 805 | His | Lys | Gly | Phe | Leu 810 | Gly | Asp | Ser | Gly | Leu 815 | Pro |
| Gly | Leu | Lys | Gly 820 | Val | His | Gly | Lys | Pro 825 | Gly | Leu | Leu | Gly | Pro 830 | Lys | Gly |
| Glu | Arg | Gly 835 | Ser | Pro | Gly | Thr | Pro 840 | Gly | Gln | Val | Gly | Gln 845 | Pro | Gly | Thr |
| Pro | Gly 850 | Ser | Ser | Gly | Pro | Tyr 855 | Gly | Ile | Lys | Gly | Lys 860 | Ser | Gly | Leu | Pro |
| Gly 865 | Ala | Pro | Gly | Phe | Pro 870 | Gly | Ile | Ser | Gly | His 875 | Pro | Gly | Lys | Lys | Gly 880 |
| Thr | Arg | Gly | Lys | Lys 885 | Gly | Pro | Pro | Gly | Ser 890 | Ile | Val | Lys | Lys | Gly 895 | Leu |
| Pro | Gly | Leu | Lys 900 | Gly | Leu | Pro | Gly | Asn 905 | Pro | Gly | Leu | Val | Gly 910 | Leu | Lys |
| Gly | Ser | Pro 915 | Gly | Ser | Pro | Gly | Val 920 | Ala | Gly | Leu | Pro | Ala 925 | Leu | Ser | Gly |
| Pro | Lys 930 | Gly | Glu | Lys | Gly | Ser 935 | Val | Gly | Phe | Val | Gly 940 | Phe | Pro | Gly | Ile |
| Pro 945 | Gly | Leu | Pro | Gly | Ile 950 | Pro | Gly | Thr | Arg | Gly 955 | Leu | Lys | Gly | Ile | Pro 960 |
| Gly | Ser | Thr | Gly | Lys 965 | Met | Gly | Pro | Ser | Gly 970 | Arg | Ala | Gly | Thr | Pro 975 | Gly |
| Glu | Lys | Gly | Asp 980 | Arg | Gly | Asn | Pro | Gly 985 | Pro | Val | Gly | Ile | Pro 990 | Ser | Pro |
| Arg | Arg | Pro 995 | Met | Ser | Asn | Leu | Trp 1000 | Leu | Lys | Gly | Asp | Lys 1005 | Gly | Ser | Gln |
| Gly | Ser | Ala 1010 | Gly | Ser | Asn | Gly | Phe 1015 | Pro | Gly | Pro | Arg | Gly 1020 | Asp | Lys | Gly |
| Glu | Ala 1025 | Gly | Arg | Pro | Gly | Pro 1030 | Pro | Gly | Leu | Pro | Gly 1035 | Ala | Pro | Gly | Leu 1040 |
| Pro | Gly | Ile | Ile | Lys 1045 | Gly | Val | Ser | Gly | Lys 1050 | Pro | Gly | Pro | Pro | Gly 1055 | Phe |
| Met | Gly | Ile | Arg 1060 | Gly | Leu | Pro | Gly | Lys 1065 | Gly | Ser | Ser | Gly | Ile 1070 | Thr |
| Gly | Phe | Pro | Gly 1075 | Met | Pro | Gly | Glu | Ser 1080 | Gly | Ser | Gln | Gly | Ile 1085 | Arg | Gly |

Ser Pro Gly Leu Pro Gly Ala Ser Gly Leu Pro Gly Leu Lys Gly Asp
              1090                1095                1100
Asn Gly Gln Thr Val Glu Ile Ser Gly Ser Pro Gly Pro Lys Gly Gln
1105                1110                1115                1120
Pro Gly Glu Ser Gly Phe Lys Gly Thr Lys Gly Arg Asp Gly Leu Ile
              1125                1130                1135
Gly Asn Ile Gly Phe Pro Gly Asn Lys Gly Glu Asp Gly Lys Val Gly
              1140                1145                1150
Val Ser Gly Asp Val Gly Leu Pro Gly Ala Pro Gly Phe Pro Gly Val
              1155                1160                1165
Ala Gly Met Arg Gly Glu Pro Gly Leu Pro Gly Ser Ser Gly His Gln
              1170                1175                1180
Gly Ala Ile Gly Pro Leu Gly Ser Pro Gly Leu Ile Gly Pro Lys Gly
1185                1190                1195                1200
Phe Pro Gly Phe Pro Gly Leu His Gly Leu Asn Gly Leu Pro Gly Thr
              1205                1210                1215
Lys Gly Thr His Gly Thr Pro Gly Pro Ser Ile Thr Gly Val Pro Gly
              1220                1225                1230
Pro Ala Gly Leu Pro Gly Pro Lys Gly Glu Lys Gly Tyr Pro Gly Ile
              1235                1240                1245
Gly Ile Gly Ala Pro Gly Lys Pro Gly Leu Arg Gly Gln Lys Gly Asp
              1250                1255                1260
Arg Gly Phe Pro Gly Leu Gln Gly Pro Ala Gly Leu Pro Gly Ala Pro
1265                1270                1275                1280
Gly Ile Ser Leu Pro Ser Leu Ile Ala Gly Gln Pro Gly Asp Pro Gly
              1285                1290                1295
Arg Pro Gly Leu Asp Gly Glu Arg Gly Arg Pro Gly Pro Ala Gly Pro
              1300                1305                1310
Pro Gly Pro Pro Gly Pro Ser Ser Asn Gln Gly Asp Thr Gly Asp Pro
              1315                1320                1325
Gly Phe Pro Gly Ile Pro Gly Pro Lys Gly Pro Lys Gly Asp Gln Gly
              1330                1335                1340
Ile Pro Gly Phe Ser Gly Leu Pro Gly Glu Leu Gly Leu Lys Gly Ser
1345                1350                1355                1360
Ser Gly Leu Gln Gly Asp Pro Gly Gln Thr Pro Thr Ala Glu Ala Val
              1365                1370                1375
Gln Val Pro Pro Gly Pro Leu Gly Leu Pro Gly Ile Asp Gly Ile Pro
              1380                1385                1390
Gly Leu Thr Gly Asp Pro Gly Ala Gln Gly Pro Val Gly Leu Gln Gly
              1395                1400                1405
Ser Lys Gly Leu Pro Gly Ile Pro Gly Lys Asp Gly Pro Ser Gly Leu
              1410                1415                1420
Pro Gly Pro Pro Gly Ala Leu Gly Asp Pro Gly Leu Pro Gly Leu Gln
1425                1430                1435                1440
Gly Pro Pro Gly Phe Glu Gly Ala Pro Gly Gln Gln Gly Pro Ser Gly
              1445                1450                1455
Cys Leu Glu Cys Leu Ala Arg Ala Glu Trp Ala Thr Arg Trp Ser Thr
              1460                1465                1470
Ala Ser Arg Asn Arg Cys Pro Arg Val Pro Ser Gly Ala Ser Cys Gly
              1475                1480                1485
Trp Gly Thr Ala Tyr Cys Leu Trp Arg Gly Asn Thr Lys Pro Thr Thr
              1490                1495                1500
Arg Thr Trp Ala Leu Leu Ala Pro Val Cys Pro Ala Ser Ala Pro Cys

| 1505 | | | | 1510 | | | | 1515 | | | | 1520 | |
|---|---|---|---|---|---|---|---|---|---|---|---|---|---|

Pro His Tyr Cys Asn Ile Asn Glu Val Cys His Tyr Ala Arg Arg Asn
                    1525                      1530                      1535

Asp Lys Ser Tyr Trp Leu Ser Thr Thr Ala Pro Ile Pro Met Met Pro
                    1540                      1545                      1550

Val Ser Gln Thr Gln Ile Pro Gln Tyr Ile Ser Arg Cys Ser Val Cys
                    1555                      1560                      1565

Glu Ala Pro Ser Lys Pro Phe Cys Ala Gln Pro Gly His His His Pro
1570                    1575                      1580

Ala Val Pro Pro Gly Leu Ala Gln Pro Leu Asp Trp Val Leu Phe Pro
1585                    1590                      1595                      1600

His Ala His Cys Arg Trp Cys Arg Gly Trp Arg Gln Ser Leu Val Ser
                    1605                      1610                      1615

Pro Gly Ser Ser Arg Thr Phe Gly Pro Leu Leu Ser Ser Asn Ala Val
                    1620                      1625                      1630

Ala Arg Gly Thr Cys His Tyr Phe Ala Asn Lys Tyr Ser Phe Trp Leu
                    1635                      1640                      1645

Thr Thr Val Glu Glu Arg Gln Gln Phe Gly Glu Leu Pro Val Ser Glu
                    1650                      1655                      1660

Thr Leu Lys Ala Gly Gln Leu His Thr Arg Val Ser Arg Cys Gln Val
1665                    1670                      1675                      1680

Cys Met Asn Arg Asn Ser Ser Trp Arg Arg Ser Leu His Ser
1685                    1690

( 2 ) INFORMATION FOR SEQ ID NO:3:

( i ) SEQUENCE CHARACTERISTICS:
        ( A ) LENGTH: 343 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
CGCAGCCTCT GCAGGCTGCC CCCAAAGACT CAGGGCCAGT AAGAACAAGC CGGCAGCCAG    60
GCTGACTCCA CGCAGTTTCA TTCTTCTCCG GCTCCCGCAG CTCCTTCAGC ACCCGCACGA   120
AATTCCCGGC TGGCTCTAAC CAATTGACAT AATCTTGAGG GTTTATATGG AGAGAGCTAG   180
AGCCGGAGAG GGACAGTGAG GCTTGGGTGA AGAGAAAGAA GCTTTTTAAG AGTGGAAGAA   240
AAAAAAACTC CCTGTCACTC CGAACCCACT TCTCTTTCTT CGAAAAATTC TCACCTTCTT   300
TTTTTTAGA AGAAGAAGAA GGAGCTACTC TTCCTTCCCC CCT                     343
```

( 2 ) INFORMATION FOR SEQ ID NO:4:

( i ) SEQUENCE CHARACTERISTICS:
        ( A ) LENGTH: 27 amino acids
        ( B ) TYPE: amino acid
        ( D ) TOPOLOGY: linear ( x i ) SEQUENCE DESCRIPTION: SEQ ID NO:4:

Ala Ala Glu Ala Pro Gln Gly Trp Leu Ser Leu Ala Leu Leu Phe Leu
1              5                    10                      15

Gly Ala Ala Leu Ser Val Gly Arg Leu Lys Met
                  20                    25

( 2 ) INFORMATION FOR SEQ ID NO:5:

( i ) SEQUENCE CHARACTERISTICS:
        ( A ) LENGTH: 115 base pairs
        ( B ) TYPE: nucleic acid ( C ) STRANDEDNESS: double
        ( D ) TOPOLOGY: linear ( x i ) SEQUENCE DESCRIPTION: SEQ ID NO:5:

TCCCTGGGCT GCTGGTCTTC TTTACCTTCC AGCTGCTCAC AGAACAGAGA GTTTCTACAT     60

ACAAGCAGAA GATGTGAAAA TATTGGGAAT AAATAAAGTA TATGCTTATA AACAA          115

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:6:

Met   Leu   Ile   Asn   Lys
    1                       5

( 2 ) INFORMATION FOR SEQ ID NO:7:

( i ) SEQUENCE CHARACTERISTICS:
        ( A ) LENGTH: 547 amino acids
        ( B ) TYPE: amino acid
        ( D ) TOPOLOGY: linear ( x i ) SEQUENCE DESCRIPTION: SEQ ID NO:7:

Met   Leu   Ile   Asn   Lys   Leu   Trp   Leu   Leu   Leu   Val   Thr   Leu   Cys   Leu   Thr
    1                       5                             10                            15

Glu   Glu   Leu   Ala   Ala   Ala   Gly   Glu   Lys   Ser   Tyr   Gly   Lys   Pro   Cys   Gly
                            20                            25                            30

Gly   Gln   Asp   Cys   Ser   Gly   Ser   Cys   Gln   Cys   Phe   Pro   Glu   Lys   Gly   Ala
                      35                            40                            45

Arg   Gly   Arg   Pro   Gly   Pro   Ile   Gly   Ile   Gln   Gly   Pro   Thr   Gly   Pro   Gln
          50                            55                            60

Gly   Phe   Thr   Gly   Ser   Thr   Gly   Leu   Ser   Gly   Leu   Lys   Gly   Glu   Arg   Gly
    65                            70                            75                            80

Phe   Pro   Gly   Leu   Leu   Gly   Pro   Tyr   Gly   Pro   Lys   Gly   Asp   Lys   Gly   Pro
                            85                            90                            95

Met   Gly   Val   Pro   Gly   Phe   Leu   Gly   Ile   Asn   Gly   Ile   Pro   Gly   His   Pro
                      100                           105                           110

Gly   Gln   Pro   Gly   Pro   Arg   Gly   Pro   Pro   Gly   Leu   Asp   Gly   Cys   Asn   Gly
                115                           120                           125

Thr   Gln   Gly   Ala   Val   Gly   Phe   Pro   Gly   Pro   Asp   Gly   Tyr   Pro   Gly   Leu
          130                           135                           140

Leu   Gly   Pro   Pro   Gly   Leu   Pro   Gly   Gln   Lys   Gly   Ser   Lys   Gly   Asp   Pro
    145                           150                           155                           160

Val   Leu   Ala   Pro   Gly   Ser   Phe   Lys   Gly   Ile   Lys   Gly   Asp   Pro   Gly   Leu
                            165                           170                           175

Pro   Gly   Leu   Asp   Gly   Ile   Thr   Gly   Pro   Gln   Gly   Ala   Pro   Gly   Phe   Pro
                      180                           185                           190

Gly   Ala   Val   Gly   Pro   Ala   Gly   Pro   Pro   Gly   Leu   Gln   Gly   Pro   Pro   Gly
                195                           200                           205

Pro   Pro   Gly   Pro   Leu   Gly   Pro   Asp   Gly   Asn   Met   Gly   Leu   Gly   Phe   Gln
          210                           215                           220

Gly   Glu   Lys   Gly   Val   Lys   Gly   Asp   Val   Gly   Leu   Pro   Gly   Pro   Ala   Gly
    225                           230                           235                           240

Pro   Pro   Pro   Ser   Thr   Gly   Glu   Leu   Glu   Phe   Met   Gly   Phe   Pro   Lys   Gly
                            245                           250                           255

```
Lys  Lys  Gly  Ser  Lys  Gly  Glu  Pro  Gly  Pro  Lys  Gly  Phe  Pro  Gly  Ile
              260                 265                      270

Ser  Gly  Pro  Pro  Gly  Phe  Pro  Gly  Leu  Gly  Thr  Thr  Gly  Glu  Lys  Gly
              275                 280                      285

Glu  Lys  Gly  Glu  Lys  Gly  Ile  Pro  Gly  Leu  Pro  Gly  Pro  Arg  Gly  Pro
         290                 295                      300

Met  Gly  Ser  Glu  Gly  Val  Gln  Gly  Pro  Pro  Gly  Gln  Gln  Gly  Lys  Lys
305                      310                 315                          320

Gly  Thr  Leu  Gly  Phe  Pro  Gly  Leu  Asn  Gly  Phe  Gln  Gly  Ile  Glu  Gly
                   325                 330                      335

Gln  Lys  Gly  Asp  Ile  Gly  Leu  Pro  Gly  Pro  Asp  Val  Phe  Ile  Asp  Ile
              340                 345                      350

Asp  Gly  Ala  Val  Ile  Ser  Gly  Asn  Pro  Gly  Asp  Pro  Gly  Val  Pro  Gly
              355                 360                      365

Leu  Pro  Gly  Leu  Lys  Gly  Asp  Glu  Gly  Ile  Gln  Gly  Leu  Arg  Gly  Pro
     370                 375                      380

Ser  Gly  Val  Pro  Gly  Leu  Pro  Ala  Leu  Ser  Gly  Val  Pro  Gly  Ala  Leu
385                      390                 395                          400

Gly  Pro  Gln  Gly  Phe  Pro  Gly  Leu  Lys  Gly  Asp  Gln  Gly  Asn  Pro  Gly
                   405                 410                      415

Arg  Thr  Thr  Ile  Gly  Ala  Ala  Gly  Leu  Pro  Gly  Arg  Asp  Gly  Leu  Pro
              420                 425                      430

Gly  Pro  Pro  Gly  Pro  Pro  Gly  Pro  Pro  Ser  Pro  Glu  Phe  Glu  Thr  Glu
              435                 440                      445

Thr  Leu  His  Asn  Lys  Glu  Ser  Gly  Phe  Pro  Gly  Leu  Arg  Gly  Glu  Gln
     450                 455                      460

Gly  Pro  Lys  Gly  Asn  Leu  Gly  Leu  Lys  Gly  Ile  Lys  Gly  Asp  Ser  Gly
465                      470                 475                          480

Phe  Cys  Ala  Cys  Asp  Gly  Gly  Val  Pro  Asn  Thr  Gly  Pro  Pro  Gly  Glu
              485                 490                      495

Pro  Gly  Pro  Pro  Gly  Pro  Trp  Gly  Leu  Ile  Gly  Leu  Pro  Gly  Leu  Lys
              500                 505                      510

Gly  Ala  Arg  Gly  Asp  Arg  Gly  Ser  Gly  Gly  Ala  Gln  Gly  Pro  Ala  Gly
              515                 520                      525

Ala  Pro  Gly  Leu  Val  Gly  Pro  Leu  Gly  Pro  Ser  Gly  Pro  Lys  Gly  Lys
     530                 535                      540

Lys  Gly  Gly
545
```

( 2 ) INFORMATION FOR SEQ ID NO:8:

( i ) SEQUENCE CHARACTERISTICS:
      ( A ) LENGTH: 549 amino acids
      ( B ) TYPE: amino acid
      ( D ) TOPOLOGY: linear ( x i ) SEQUENCE DESCRIPTION: SEQ ID NO:8:

```
Met  Gly  Arg  Asp  Gln  Arg  Ala  Val  Ala  Gly  Pro  Ala  Leu  Arg  Arg  Trp
1                   5                        10                           15

Leu  Leu  Leu  Gly  Thr  Val  Thr  Val  Gly  Phe  Leu  Ala  Gln  Ser  Val  Leu
              20                  25                      30

Ala  Gly  Val  Lys  Lys  Phe  Asp  Val  Pro  Cys  Gly  Gly  Arg  Asp  Cys  Ser
              35                  40                      45

Gly  Gly  Cys  Gln  Cys  Tyr  Pro  Glu  Lys  Gly  Gly  Arg  Gly  Gln  Pro  Gly
         50                  55                      60

Pro  Val  Gly  Pro  Gln  Gly  Tyr  Asn  Gly  Pro  Pro  Gly  Leu  Gln  Gly  Phe
```

```
          65                      70                      75                      80
Pro  Gly  Leu  Gln  Gly  Arg  Lys  Gly  Asp  Lys  Gly  Glu  Arg  Gly  Ala  Pro
                    85                      90                      95
Gly  Val  Thr  Gly  Pro  Lys  Gly  Asp  Val  Gly  Ala  Arg  Gly  Val  Ser  Gly
               100                     105                     110
Phe  Pro  Gly  Ala  Asp  Gly  Ile  Pro  Gly  His  Pro  Gly  Gln  Gly  Gly  Pro
          115                     120                     125
Arg  Gly  Arg  Pro  Gly  Tyr  Asp  Gly  Cys  Asn  Gly  Thr  Gln  Gly  Asp  Ser
     130                     135                     140
Gly  Pro  Gln  Gly  Pro  Pro  Gly  Ser  Glu  Gly  Phe  Thr  Gly  Pro  Pro  Gly
145                     150                     155                     160
Pro  Gln  Gly  Pro  Lys  Gly  Gln  Lys  Gly  Glu  Pro  Tyr  Ala  Leu  Pro  Lys
                    165                     170                     175
Glu  Glu  Arg  Asp  Arg  Tyr  Arg  Gly  Glu  Pro  Gly  Glu  Pro  Gly  Leu  Val
               180                     185                     190
Gly  Phe  Gln  Gly  Pro  Pro  Gly  Arg  Pro  Gly  His  Val  Gly  Gln  Met  Gly
          195                     200                     205
Pro  Val  Gly  Ala  Pro  Gly  Arg  Pro  Gly  Pro  Pro  Gly  Pro  Pro  Gly  Pro
     210                     215                     220
Lys  Gly  Gln  Gln  Gly  Asn  Arg  Gly  Leu  Gly  Phe  Tyr  Gly  Val  Lys  Gly
225                     230                     235                     240
Glu  Lys  Gly  Asp  Val  Gly  Gln  Pro  Gly  Pro  Asn  Gly  Ile  Pro  Ser  Asp
                    245                     250                     255
Thr  Leu  His  Pro  Ile  Ile  Ala  Pro  Thr  Gly  Val  Thr  Phe  His  Pro  Asp
               260                     265                     270
Gln  Tyr  Lys  Gly  Glu  Lys  Gly  Ser  Glu  Gly  Glu  Pro  Gly  Ile  Arg  Gly
          275                     280                     285
Ile  Ser  Leu  Lys  Gly  Glu  Glu  Gly  Ile  Met  Gly  Phe  Pro  Gly  Leu  Arg
     290                     295                     300
Gly  Tyr  Pro  Gly  Leu  Ser  Gly  Glu  Lys  Gly  Ser  Pro  Gly  Gln  Lys  Gly
305                     310                     315                     320
Ser  Arg  Gly  Leu  Asp  Gly  Tyr  Gln  Gly  Pro  Asp  Gly  Pro  Arg  Gly  Pro
                    325                     330                     335
Lys  Gly  Glu  Ala  Gly  Asp  Pro  Gly  Pro  Pro  Gly  Leu  Pro  Ala  Tyr  Ser
               340                     345                     350
Pro  His  Pro  Ser  Leu  Ala  Lys  Gly  Ala  Arg  Gly  Asp  Pro  Gly  Phe  Pro
          355                     360                     365
Gly  Ala  Gln  Gly  Glu  Pro  Gly  Ser  Gln  Gly  Glu  Pro  Gly  Asp  Pro  Gly
     370                     375                     380
Leu  Pro  Gly  Pro  Pro  Gly  Leu  Ser  Ile  Gly  Asp  Gly  Asp  Gln  Arg  Arg
385                     390                     395                     400
Gly  Leu  Pro  Gly  Glu  Met  Gly  Pro  Lys  Gly  Phe  Ile  Gly  Asp  Pro  Gly
                    405                     410                     415
Ile  Pro  Ala  Leu  Tyr  Gly  Gly  Pro  Pro  Gly  Pro  Asp  Gly  Lys  Arg  Gly
               420                     425                     430
Pro  Pro  Gly  Pro  Pro  Gly  Leu  Pro  Gly  Pro  Pro  Gly  Pro  Asp  Gly  Phe
          435                     440                     445
Leu  Phe  Gly  Leu  Lys  Gly  Ala  Lys  Gly  Arg  Ala  Gly  Phe  Pro  Gly  Leu
     450                     455                     460
Pro  Gly  Ser  Pro  Gly  Ala  Arg  Gly  Pro  Lys  Gly  Trp  Lys  Gly  Asp  Ala
465                     470                     475                     480
Gly  Glu  Cys  Arg  Cys  Thr  Glu  Gly  Asp  Glu  Ala  Ile  Lys  Gly  Leu  Pro
                    485                     490                     495
```

```
Gly  Leu  Pro  Gly  Pro  Lys  Gly  Phe  Ala  Gly  Ile  Asn  Gly  Glu  Pro  Gly
               500                      505                      510

Arg  Lys  Gly  Asp  Lys  Gly  Asp  Pro  Gly  Gln  His  Gly  Leu  Pro  Gly  Phe
          515                      520                      525

Pro  Gly  Leu  Lys  Gly  Val  Pro  Gly  Asn  Ile  Gly  Ala  Pro  Gly  Pro  Lys
     530                      535                      540

Gly  Ala  Lys  Gly  Asp
545
```

( 2 ) INFORMATION FOR SEQ ID NO:9:

( i ) SEQUENCE CHARACTERISTICS:
      ( A ) LENGTH: 532 amino acids
      ( B ) TYPE: amino acid
      ( D ) TOPOLOGY: linear ( x i ) SEQUENCE DESCRIPTION: SEQ ID NO:9:

```
Met  Gly  Pro  Arg  Leu  Ser  Val  Trp  Leu  Leu  Leu  Pro  Ala  Ala  Leu
1                   5                        10                      15

Leu  Leu  His  Glu  Glu  His  Ser  Arg  Ala  Ala  Ala  Lys  Gly  Gly  Cys  Ala
               20                      25                      30

Gly  Ser  Gly  Cys  Gly  Lys  Cys  Asp  Cys  His  Gly  Val  Lys  Gly  Gln  Lys
          35                      40                      45

Gly  Glu  Arg  Gly  Leu  Pro  Gly  Leu  Gln  Gly  Val  Ile  Gly  Phe  Pro  Gly
     50                      55                      60

Met  Gln  Gly  Pro  Glu  Gly  Pro  Gln  Gly  Pro  Pro  Gly  Gln  Lys  Gly  Asp
65                      70                      75                      80

Thr  Gly  Glu  Pro  Gly  Leu  Pro  Gly  Thr  Lys  Gly  Thr  Arg  Gly  Pro  Pro
                    85                      90                      95

Gly  Ala  Ser  Gly  Tyr  Pro  Gly  Asn  Pro  Gly  Leu  Pro  Gly  Ile  Pro  Gly
               100                     105                     110

Gln  Asp  Gly  Pro  Pro  Gly  Pro  Pro  Gly  Ile  Pro  Gly  Cys  Asn  Gly  Thr
          115                     120                     125

Lys  Gly  Glu  Arg  Gly  Pro  Leu  Gly  Pro  Pro  Gly  Leu  Pro  Gly  Phe  Ala
     130                     135                     140

Gly  Asn  Pro  Gly  Pro  Pro  Gly  Leu  Pro  Gly  Met  Lys  Gly  Asp  Pro  Gly
145                     150                     155                     160

Glu  Ile  Leu  Gly  His  Val  Pro  Gly  Met  Leu  Leu  Lys  Gly  Glu  Arg  Gly
                    165                     170                     175

Phe  Pro  Gly  Ile  Pro  Gly  Thr  Pro  Gly  Pro  Pro  Gly  Leu  Pro  Gly  Leu
               180                     185                     190

Gln  Gly  Pro  Val  Gly  Pro  Pro  Gly  Phe  Thr  Gly  Pro  Pro  Gly  Pro  Pro
          195                     200                     205

Gly  Pro  Pro  Gly  Pro  Pro  Gly  Glu  Lys  Gly  Gln  Met  Gly  Leu  Ser  Phe
     210                     215                     220

Gln  Gly  Pro  Lys  Gly  Asp  Lys  Gly  Asp  Gln  Gly  Val  Ser  Gly  Pro  Pro
225                     230                     235                     240

Gly  Val  Pro  Gly  Gln  Ala  Gln  Val  Gln  Glu  Lys  Gly  Asp  Phe  Ala  Thr
                    245                     250                     255

Lys  Gly  Glu  Lys  Gly  Gln  Lys  Gly  Glu  Pro  Gly  Phe  Gln  Gly  Met  Pro
               260                     265                     270

Gly  Val  Gly  Glu  Lys  Gly  Glu  Pro  Gly  Lys  Pro  Gly  Pro  Arg  Gly  Lys
          275                     280                     285

Pro  Gly  Lys  Asp  Gly  Asp  Lys  Gly  Glu  Lys  Gly  Ser  Pro  Gly  Phe  Pro
     290                     295                     300

Gly  Glu  Pro  Gly  Tyr  Pro  Gly  Leu  Ile  Gly  Arg  Gln  Gly  Pro  Ala  Gly
```

-continued

| | 305 | | | | 310 | | | | 315 | | | | 320 |
|---|---|---|---|---|---|---|---|---|---|---|---|---|---|
| Glu | Lys | Gly | Glu | Ala | Gly | Pro | Pro | Gly | Pro | Gly | Ile | Val | Ile | Gly |
| | | | | 325 | | | | 330 | | | | 335 | |
| Thr | Gly | Pro | Leu | Gly | Glu | Lys | Gly | Glu | Arg | Gly | Tyr | Pro | Gly | Thr | Pro |
| | | | 340 | | | | 345 | | | | 350 | | |
| Gly | Pro | Arg | Gly | Glu | Pro | Gly | Pro | Lys | Gly | Phe | Pro | Gly | Leu | Pro | Gly |
| | | 355 | | | | 360 | | | | 365 | | | |
| Gln | Pro | Gly | Pro | Pro | Gly | Leu | Pro | Val | Pro | Gly | Gln | Ala | Gly | Ala | Pro |
| | 370 | | | | 375 | | | | 380 | | | | |
| Gly | Phe | Pro | Gly | Glu | Arg | Gly | Glu | Lys | Gly | Asp | Arg | Gly | Phe | Pro | Gly |
| 385 | | | | 390 | | | | 395 | | | | 400 | |
| Thr | Ser | Leu | Pro | Gly | Pro | Ser | Gly | Arg | Asp | Gly | Leu | Pro | Gly | Pro | Pro |
| | | | | 405 | | | | 410 | | | | 415 | |
| Gly | Ser | Pro | Gly | Pro | Pro | Gly | Gln | Pro | Gly | Tyr | Thr | Asn | Gly | Ile | Val |
| | | | 420 | | | | 425 | | | | 430 | | |
| Glu | Cys | Gln | Pro | Gly | Pro | Pro | Gly | Asp | Gln | Gly | Pro | Pro | Gly | Ile | Pro |
| | | 435 | | | | 440 | | | | 445 | | | |
| Gly | Gln | Pro | Gly | Phe | Ile | Gly | Glu | Ile | Gly | Glu | Lys | Gly | Gln | Lys | Gly |
| | 450 | | | | 455 | | | | 460 | | | | |
| Glu | Ser | Cys | Leu | Ile | Cys | Asp | Ile | Asp | Gly | Tyr | Arg | Gly | Pro | Pro | Gly |
| 465 | | | | 470 | | | | 475 | | | | 480 | |
| Pro | Gln | Gly | Pro | Pro | Gly | Glu | Ile | Gly | Phe | Pro | Gly | Gln | Pro | Gly | Ala |
| | | | 485 | | | | 490 | | | | 495 | | |
| Lys | Gly | Asp | Arg | Gly | Leu | Pro | Gly | Arg | Asp | Gly | Val | Ala | Gly | Val | Pro |
| | | 500 | | | | 505 | | | | 510 | | | |
| Gly | Pro | Gln | Gly | Thr | Pro | Gly | Leu | Ile | Gly | Gln | Pro | Gly | Ala | Lys | Gly |
| | | 515 | | | | 520 | | | | 525 | | | |
| Glu | Pro | Gly | Glu |
| | 530 | | |

( 2 ) INFORMATION FOR SEQ ID NO:10:

( i ) SEQUENCE CHARACTERISTICS:
  ( A ) LENGTH: 546 amino acids
  ( B ) TYPE: amino acid
  ( D ) TOPOLOGY: linear ( x i ) SEQUENCE DESCRIPTION: SEQ ID NO:10:

| Met | Lys | Leu | Arg | Gly | Val | Ser | Leu | Ala | Ala | Gly | Leu | Phe | Leu | Leu | Ala |
|---|---|---|---|---|---|---|---|---|---|---|---|---|---|---|---|
| 1 | | | | 5 | | | | | 10 | | | | | 15 | |
| Leu | Ser | Leu | Trp | Gly | Gln | Pro | Ala | Glu | Ala | Ala | Ala | Cys | Tyr | Gly | Cys |
| | | | 20 | | | | | 25 | | | | | 30 | | |
| Ser | Pro | Gly | Ser | Lys | Cys | Asp | Cys | Ser | Gly | Ile | Lys | Gly | Glu | Lys | Gly |
| | | 35 | | | | 40 | | | | 45 | | | | | |
| Glu | Arg | Gly | Phe | Pro | Gly | Leu | Glu | Gly | His | Pro | Gly | Leu | Pro | Gly | Phe |
| | 50 | | | | 55 | | | | 60 | | | | | | |
| Pro | Gly | Pro | Glu | Gly | Pro | Pro | Gly | Pro | Arg | Gly | Gln | Lys | Gly | Asp | Asp |
| 65 | | | | 70 | | | | 75 | | | | 80 | | | |
| Gly | Ile | Pro | Gly | Pro | Pro | Gly | Pro | Lys | Gly | Ile | Arg | Gly | Pro | Pro | Gly |
| | | | | 85 | | | | 90 | | | | 95 | | | |
| Leu | Pro | Gly | Phe | Pro | Gly | Thr | Pro | Gly | Leu | Pro | Gly | Met | Pro | Gly | His |
| | | | 100 | | | | 105 | | | | 110 | | | | |
| Asp | Gly | Ala | Pro | Gly | Pro | Gln | Gly | Ile | Pro | Gly | Cys | Asn | Gly | Thr | Lys |
| | | | 115 | | | | 120 | | | | 125 | | | | |
| Gly | Glu | Arg | Gly | Phe | Pro | Gly | Ser | Pro | Gly | Phe | Pro | Gly | Leu | Gln | Gly |
| | | | 130 | | | | 135 | | | | 140 | | | | |

-continued

| | | | | | | | | | | | | | | | |
|---|---|---|---|---|---|---|---|---|---|---|---|---|---|---|---|
| Pro 145 | Pro | Gly | Pro | Pro | Gly 150 | Ile | Pro | Gly | Met | Lys 155 | Gly | Glu | Pro | Gly | Ser 160 |
| Ile | Ile | Met | Ser | Ser 165 | Leu | Pro | Gly | Pro | Lys 170 | Gly | Asn | Pro | Gly | Tyr 175 | Pro |
| Gly | Pro | Pro | Gly 180 | Ile | Gln | Gly | Leu | Pro 185 | Gly | Pro | Thr | Gly | Ile 190 | Pro | Gly |
| Pro | Ile | Gly 195 | Pro | Pro | Gly | Pro | Pro 200 | Gly | Leu | Met | Gly | Pro 205 | Pro | Gly | Pro |
| Pro | Gly 210 | Leu | Pro | Gly | Pro | Lys 215 | Gly | Asn | Met | Gly | Leu 220 | Asn | Phe | Gln | Gly |
| Pro 225 | Lys | Gly | Glu | Lys | Gly 230 | Glu | Gln | Gly | Leu | Gln 235 | Gly | Pro | Pro | Gly | Pro 240 |
| Pro | Gly | Gln | Ile | Ser 245 | Glu | Gln | Lys | Arg | Pro 250 | Ile | Asp | Val | Glu | Phe 255 | Gln |
| Lys | Gly | Asp | Gln 260 | Gly | Leu | Pro | Gly | Asp 265 | Arg | Gly | Pro | Pro | Gly 270 | Pro | Pro |
| Gly | Ile | Arg 275 | Gly | Pro | Pro | Gly | Pro 280 | Pro | Gly | Gly | Glu | Lys 285 | Gly | Glu | Lys |
| Gly | Glu 290 | Gln | Gly | Glu | Pro | Gly 295 | Lys | Arg | Gly | Lys | Pro 300 | Gly | Lys | Asp | Gly |
| Glu 305 | Asn | Gly | Gln | Pro | Gly 310 | Ile | Pro | Gly | Leu | Pro 315 | Gly | Asp | Pro | Gly | Tyr 320 |
| Pro | Gly | Glu | Pro | Gly 325 | Arg | Asp | Gly | Glu | Lys 330 | Gly | Gln | Lys | Gly | Asp 335 | Thr |
| Gly | Pro | Pro | Gly 340 | Pro | Pro | Gly | Leu | Val 345 | Ile | Pro | Arg | Pro | Gly 350 | Thr | Gly |
| Ile | Thr | Ile 355 | Gly | Glu | Lys | Gly | Asn 360 | Ile | Gly | Leu | Pro | Gly 365 | Leu | Pro | Gly |
| Glu | Lys 370 | Gly | Glu | Arg | Gly | Phe 375 | Pro | Gly | Ile | Gln | Gly 380 | Pro | Pro | Gly | Leu |
| Pro 385 | Gly | Pro | Pro | Gly | Ala 390 | Ala | Val | Met | Gly | Pro 395 | Pro | Gly | Pro | Pro | Gly 400 |
| Phe | Pro | Gly | Glu | Arg 405 | Gly | Gln | Lys | Gly | Asp 410 | Glu | Gly | Pro | Pro | Gly 415 | Ile |
| Ser | Ile | Pro | Gly 420 | Pro | Pro | Gly | Leu | Asp 425 | Gly | Gln | Pro | Gly | Ala 430 | Pro | Gly |
| Leu | Pro | Gly 435 | Pro | Pro | Gly | Pro | Ala 440 | Gly | Pro | His | Ile | Pro 445 | Pro | Ser | Asp |
| Glu | Ile 450 | Cys | Glu | Pro | Gly | Pro 455 | Pro | Gly | Pro | Pro | Gly 460 | Ser | Pro | Gly | Asp |
| Lys 465 | Gly | Leu | Gln | Gly | Glu 470 | Gln | Gly | Val | Lys | Gly 475 | Asp | Lys | Gly | Asp | Thr 480 |
| Cys | Phe | Asn | Cys | Ile 485 | Gly | Thr | Gly | Ile | Ser 490 | Gly | Pro | Pro | Gly | Gln 495 | Pro |
| Gly | Leu | Pro | Gly 500 | Leu | Pro | Gly | Pro | Pro 505 | Gly | Ser | Leu | Gly | Phe 510 | Pro | Gly |
| Gln | Lys | Gly 515 | Glu | Lys | Gly | Gln | Ala 520 | Gly | Ala | Thr | Gly | Pro 525 | Lys | Gly | Leu |
| Pro | Gly 530 | Ile | Pro | Gly | Ala | Pro 535 | Gly | Ala | Pro | Gly | Phe 540 | Pro | Gly | Ser | Lys |
| Gly 545 | Glu | | | | | | | | | | | | | | |

What is claimed is:

1. An isolated polynucleotide encoding a human α-6(IV) collagen.

2. An isolated polynucleotide according to claim 1, wherein the DNA sequence of said polynucleotide is the DNA shown in FIGS. 1A–1Q (SEQ ID NO: 1), or an RNA sequence wherein said DNA sequence is modified by replacing each "T" with "U".

3. An isolated polynucleotide according to claim 1, wherein the amino acid sequence of said collagen is the polypeptide shown in FIGS. 1A–1Q (SEQ ID NO: 2).

4. An isolated polynucleotide according to claim 1, wherein the amino acid sequence of said collagen is the polypeptide shown in FIGS. 1A–1Q (SEQ ID NO: 2), spanning amino acids 1–1460 inclusive.

5. An isolated polynucleotide, wherein said polynucleotide contains at least thirty nucleotide residues and hybridizes under stringent conditions to a DNA sequence shown in FIGS. 1A–1Q (SEQ ID NO: 1), or an RNA sequence wherein said sequence is modified by replacing each "T" with "U".

6. An isolated polynucleotide according to claim 5, wherein said polynucleotide contains at least forty nucleotide residues.

7. An isolated polynucleotide according to claim 5, wherein said polynucleotide contains at least fifty nucleotide residues.

8. A vector comprising a plasmid containing an isolated polynucleotide according to claim 1.

* * * * *